United States Patent
el Kaliouby et al.

(10) Patent No.: US 10,517,521 B2
(45) Date of Patent: *Dec. 31, 2019

(54) MENTAL STATE MOOD ANALYSIS USING HEART RATE COLLECTION BASED ON VIDEO IMAGERY

(71) Applicant: Affectiva, Inc., Boston, MA (US)

(72) Inventors: Rana el Kaliouby, Milton, MA (US); Viprali Bhatkar, Cambridge, MA (US); Niels Haering, Reston, MA (US); Youssef Kashef, Obour (EG); Ahmed Adel Osman, New Cairo (EG)

(73) Assignee: Affectiva, Inc., Boston, MA (US)

( * ) Notice: Subject to any disclaimer, the term of this patent is extended or adjusted under 35 U.S.C. 154(b) by 250 days.

This patent is subject to a terminal disclaimer.

(21) Appl. No.: 15/589,959

(22) Filed: May 8, 2017

(65) Prior Publication Data

US 2017/0238860 A1 Aug. 24, 2017

Related U.S. Application Data

(63) Continuation-in-part of application No. 14/214,719, filed on Mar. 15, 2014, now Pat. No. 9,642,536, (Continued)

(51) Int. Cl.
*G06K 9/00* (2006.01)
*A61B 5/16* (2006.01)
(Continued)

(52) U.S. Cl.
CPC ............ *A61B 5/165* (2013.01); *A61B 5/0077* (2013.01); *A61B 5/02055* (2013.01);
(Continued)

(58) Field of Classification Search
None
See application file for complete search history.

(56) References Cited

U.S. PATENT DOCUMENTS

| | | | |
|---|---|---|---|
| 3,034,500 A | 5/1962 | Backster, Jr. | |
| 3,548,806 A | 12/1970 | Fisher | |
| 3,870,034 A | 3/1975 | James | |
| 4,353,375 A | 10/1982 | Colburn et al. | |
| 4,448,203 A | 5/1984 | Williamson et al. | |
| 4,794,533 A | 12/1988 | Cohen | |

(Continued)

FOREIGN PATENT DOCUMENTS

| | | |
|---|---|---|
| JP | 08115367 | 7/1996 |
| KR | 10-2005-0021759 A | 3/2005 |
| KR | 10-2008-0016303 A | 2/2008 |
| KR | 1020100048688 A | 5/2010 |
| WO | WO 2011/045422 A1 | 4/2011 |

OTHER PUBLICATIONS

Osman et al ("Supervised Learning Approach to Remote Heart Rate Estimation from Facial Videos", 2015 11th IEEE conference, Jul. 23, 2015) (Year: 2015).*

(Continued)

*Primary Examiner* — Shervin K Nakhjavan
(74) *Attorney, Agent, or Firm* — Adams Intellex, PLC

(57) ABSTRACT

Video of one or more people is obtained and analyzed. Heart rate information is determined from the video. The heart rate information is used in mental state analysis. The heart rate information and resulting mental state analysis are correlated to stimuli, such as digital media, which is consumed or with which a person interacts. The heart rate information is used to infer mental states. The inferred mental states are used to output a mood measurement. The mental state analysis, based on the heart rate information, is used to optimize digital media or modify a digital game. Training is employed in the analysis. Machine learning is engaged to facilitate the training.

29 Claims, 19 Drawing Sheets

Related U.S. Application Data which is a continuation-in-part of application No. 13/153,745, filed on Jun. 6, 2011, now abandoned, application No. 15/589,959, which is a continuation-in-part of application No. 15/382,087, filed on Dec. 16, 2016, which is a continuation-in-part of application No. 13/153,745, filed on Jun. 6, 2011, now abandoned, said application No. 15/382,087 is a continuation-in-part of application No. 15/262,197, filed on Sep. 12, 2016, now abandoned, which is a continuation-in-part of application No. 14/796,419, filed on Jul. 10, 2015, now abandoned, which is a continuation-in-part of application No. 13/153,745, filed on Jun. 6, 2011, now abandoned, said application No. 14/796,419 is a continuation-in-part of application No. 14/460,915, filed on Aug. 15, 2014, which is a continuation-in-part of application No. 13/153,745, filed on Jun. 6, 2011, now abandoned.

(60) Provisional application No. 62/370,421, filed on Aug. 3, 2016, provisional application No. 62/469,591, filed on Mar. 10, 2017, provisional application No. 61/793,761, filed on Mar. 15, 2013, provisional application No. 61/789,038, filed on Mar. 15, 2013, provisional application No. 61/790,461, filed on Mar. 15, 2013, provisional application No. 61/798,731, filed on Mar. 15, 2013, provisional application No. 61/844,478, filed on Jul. 10, 2013, provisional application No. 61/916,190, filed on Dec. 14, 2013, provisional application No. 61/924,252, filed on Jan. 7, 2014, provisional application No. 61/927,481, filed on Jan. 15, 2014, provisional application No. 61/352,166, filed on Jun. 7, 2010, provisional application No. 61/388,002, filed on Sep. 30, 2010, provisional application No. 61/414,451, filed on Nov. 17, 2010, provisional application No. 61/439,913, filed on Feb. 6, 2011, provisional application No. 61/447,089, filed on Feb. 27, 2011, provisional application No. 61/447,464, filed on Feb. 28, 2011, provisional application No. 61/467,209, filed on Mar. 24, 2011, provisional application No. 62/217,872, filed on Sep. 12, 2015, provisional application No. 62/222,518, filed on Sep. 23, 2015, provisional application No. 62/265,937, filed on Dec. 10, 2015, provisional application No. 62/273,896, filed on Dec. 31, 2015, provisional application No. 62/301,558, filed on Feb. 29, 2016, provisional application No. 62/370,421, filed on Aug. 3, 2016, provisional application No. 62/023,800, filed on Jul. 11, 2014, provisional application No. 62/047,508, filed on Sep. 8, 2014, provisional application No. 62/082,579, filed on Nov. 20, 2014, provisional application No. 62/128,974, filed on Mar. 5, 2015, provisional application No. 61/867,007, filed on Aug. 16, 2013, provisional application No. 61/953,878, filed on Mar. 16, 2014, provisional application No. 61/972,314, filed on Mar. 30, 2014.

(51) Int. Cl.

| | | |
|---|---|---|
| *A61B 5/00* | (2006.01) | |
| *A61B 5/026* | (2006.01) | |
| *A61B 5/0295* | (2006.01) | |
| *A61B 5/0205* | (2006.01) | |
| *A61B 5/1171* | (2016.01) | |
| *G16H 50/20* | (2018.01) | |
| *G16H 30/40* | (2018.01) | |
| *G16H 20/70* | (2018.01) | |
| *A61B 5/024* | (2006.01) | |
| *A61B 5/053* | (2006.01) | |
| *A61B 5/08* | (2006.01) | |
| *A61B 5/11* | (2006.01) | |
| *G06Q 30/02* | (2012.01) | |

(52) U.S. Cl.
CPC .......... *A61B 5/0261* (2013.01); *A61B 5/0295* (2013.01); *A61B 5/1176* (2013.01); *A61B 5/7246* (2013.01); *A61B 5/7267* (2013.01); *A61B 5/7278* (2013.01); *G16H 20/70* (2018.01); *G16H 30/40* (2018.01); *G16H 50/20* (2018.01); *A61B 5/02405* (2013.01); *A61B 5/02416* (2013.01); *A61B 5/0531* (2013.01); *A61B 5/08* (2013.01); *A61B 5/1114* (2013.01); *A61B 5/441* (2013.01); *A61B 2562/0233* (2013.01); *A61B 2576/00* (2013.01); *G06Q 30/0242* (2013.01); *G06Q 30/0271* (2013.01)

(56) References Cited

U.S. PATENT DOCUMENTS

| | | |
|---|---|---|
| 4,807,642 A | 2/1989 | Brown |
| 4,817,628 A | 4/1989 | Zealear et al. |
| 4,950,069 A | 8/1990 | Hutchinson |
| 4,964,411 A | 10/1990 | Johnson et al. |
| 5,016,282 A | 5/1991 | Tomono et al. |
| 5,031,228 A | 7/1991 | Lu |
| 5,219,322 A | 6/1993 | Weathers |
| 5,247,938 A | 9/1993 | Silverstein et al. |
| 5,259,390 A | 11/1993 | Maclean |
| 5,507,291 A | 4/1996 | Stirbl et al. |
| 5,572,596 A | 11/1996 | Wildes et al. |
| 5,619,571 A | 4/1997 | Sandstorm et al. |
| 5,647,834 A | 7/1997 | Ron |
| 5,649,061 A | 7/1997 | Smyth |
| 5,663,900 A | 9/1997 | Bhandari et al. |
| 5,666,215 A | 9/1997 | Fredlund et al. |
| 5,725,472 A | 3/1998 | Weathers |
| 5,741,217 A | 4/1998 | Gero |
| 5,760,917 A | 6/1998 | Sheridan |
| 5,762,611 A | 6/1998 | Lewis et al. |
| 5,772,508 A | 6/1998 | Sugita et al. |
| 5,772,591 A | 6/1998 | Cram |
| 5,774,591 A | 6/1998 | Black et al. |
| 5,802,220 A | 9/1998 | Black et al. |
| 5,825,355 A | 10/1998 | Palmer et al. |
| 5,886,683 A | 3/1999 | Tognazzini et al. |
| 5,898,423 A | 4/1999 | Tognazzini et al. |
| 5,920,477 A | 7/1999 | Hoffberg et al. |
| 5,945,988 A | 8/1999 | Williams et al. |
| 5,959,621 A | 9/1999 | Nawaz et al. |
| 5,969,755 A | 10/1999 | Courtney |
| 5,983,129 A | 11/1999 | Cowan et al. |
| 5,987,415 A | 11/1999 | Breese et al. |
| 6,004,061 A | 12/1999 | Manico et al. |
| 6,004,312 A | 12/1999 | Finneran et al. |
| 6,008,817 A | 12/1999 | Gilmore, Jr. |
| 6,026,321 A | 2/2000 | Miyata et al. |
| 6,026,322 A | 2/2000 | Korenman et al. |
| 6,056,781 A | 5/2000 | Wassick et al. |
| 6,067,565 A | 5/2000 | Horvitz |
| 6,088,040 A | 7/2000 | Oda et al. |
| 6,091,334 A | 7/2000 | Galiana et al. |
| 6,099,319 A | 8/2000 | Zaltman et al. |
| 6,134,644 A | 10/2000 | Mayuzumi et al. |
| 6,182,098 B1 | 1/2001 | Selker |
| 6,185,534 B1 | 2/2001 | Breese et al. |
| 6,195,651 B1 | 2/2001 | Handel et al. |
| 6,212,502 B1 | 4/2001 | Ballet al. |
| 6,222,607 B1 | 4/2001 | Szajewski et al. |
| 6,309,342 B1 | 10/2001 | Blazey et al. |
| 6,327,580 B1 | 12/2001 | Pierce et al. |
| 6,349,290 B1 | 2/2002 | Horowitz et al. |
| 6,351,273 B1 | 2/2002 | Lemelson et al. |

(56) References Cited

U.S. PATENT DOCUMENTS

| | | | |
|---|---|---|---|
| 6,437,758 B1 | 8/2002 | Nielsen et al. |
| 6,443,840 B2 | 9/2002 | Von Kohorn |
| 6,530,082 B1 | 3/2003 | Del Sesto et al. |
| 6,577,329 B1 | 6/2003 | Flickner et al. |
| 6,606,102 B1 | 8/2003 | Odom |
| 6,629,104 B1 | 9/2003 | Parulski et al. |
| 6,792,458 B1 | 9/2004 | Muret et al. |
| 6,847,376 B2 | 1/2005 | Engeldrum et al. |
| 7,003,135 B2 | 2/2006 | Hsieh et al. |
| 7,013,478 B1 | 3/2006 | Hendricks et al. |
| 7,113,916 B1 | 9/2006 | Hill |
| 7,120,880 B1 | 10/2006 | Dryer et al. |
| 7,197,459 B1 | 3/2007 | Harinarayan et al. |
| 7,233,684 B2 | 6/2007 | Fedorovskaya et al. |
| 7,246,081 B2 | 7/2007 | Hill |
| 7,263,474 B2 | 8/2007 | Fables et al. |
| 7,266,582 B2 | 9/2007 | Stelting |
| 7,307,636 B2 | 12/2007 | Matraszek et al. |
| 7,319,779 B1 | 1/2008 | Mummareddy et al. |
| 7,327,505 B2 | 2/2008 | Fedorovskaya et al. |
| 7,350,138 B1 | 3/2008 | Swaminathan et al. |
| 7,353,399 B2 | 4/2008 | Ooi et al. |
| 7,355,627 B2 | 4/2008 | Yamazaki et al. |
| 7,428,318 B1 | 9/2008 | Madsen et al. |
| 7,474,801 B2 | 1/2009 | Teo et al. |
| 7,496,622 B2 | 2/2009 | Brown et al. |
| 7,549,161 B2 | 6/2009 | Poo et al. |
| 7,551,755 B1 | 6/2009 | Steinberg et al. |
| 7,555,148 B1 | 6/2009 | Steinberg et al. |
| 7,558,408 B1 | 7/2009 | Steinberg et al. |
| 7,564,994 B1 | 7/2009 | Steinberg et al. |
| 7,573,439 B2 | 8/2009 | Lau et al. |
| 7,580,512 B2 | 8/2009 | Batni et al. |
| 7,584,435 B2 | 9/2009 | Bailey et al. |
| 7,587,068 B1 | 9/2009 | Steinberg et al. |
| 7,610,289 B2 | 10/2009 | Muret et al. |
| 7,620,934 B2 | 11/2009 | Falter et al. |
| 7,644,375 B1 | 1/2010 | Anderson et al. |
| 7,676,574 B2 | 3/2010 | Glommen et al. |
| 7,757,171 B1 | 7/2010 | Wong et al. |
| 7,826,657 B2 | 11/2010 | Zhang et al. |
| 7,830,570 B2 | 11/2010 | Morita et al. |
| 7,881,493 B1 | 2/2011 | Edwards et al. |
| 7,921,036 B1 | 4/2011 | Sharma |
| 8,010,458 B2 | 8/2011 | Galbreath et al. |
| 8,022,831 B1 | 9/2011 | Wood-Eyre |
| 8,219,438 B1 | 7/2012 | Moon et al. |
| 8,239,000 B1 | 8/2012 | Morris et al. |
| 8,401,248 B1 | 3/2013 | Moon et al. |
| 8,442,638 B2 | 5/2013 | Libbus et al. |
| 8,522,779 B2 | 9/2013 | Lee et al. |
| 8,600,120 B2 | 12/2013 | Gonion et al. |
| 8,640,021 B2 | 1/2014 | Perez et al. |
| 2001/0033286 A1 | 10/2001 | Stokes et al. |
| 2001/0041021 A1 | 11/2001 | Boyle et al. |
| 2002/0007249 A1 | 1/2002 | Cranley |
| 2002/0030665 A1 | 3/2002 | Ano |
| 2002/0042557 A1 | 4/2002 | Bensen et al. |
| 2002/0054174 A1 | 5/2002 | Abbott et al. |
| 2002/0084902 A1 | 7/2002 | Zadrozny et al. |
| 2002/0171551 A1 | 11/2002 | Eshelman |
| 2002/0182574 A1 | 12/2002 | Freer |
| 2003/0035567 A1 | 2/2003 | Chang et al. |
| 2003/0037041 A1 | 2/2003 | Hertz |
| 2003/0060728 A1 | 3/2003 | Mandigo |
| 2003/0093784 A1 | 5/2003 | Dimitrova et al. |
| 2003/0191682 A1 | 10/2003 | Shepard et al. |
| 2003/0191816 A1 | 10/2003 | Landress et al. |
| 2004/0181457 A1 | 9/2004 | Biebesheimer |
| 2004/0236236 A1 | 11/2004 | Yanagidaira et al. |
| 2005/0187437 A1 | 8/2005 | Matsugu |
| 2005/0283055 A1 | 12/2005 | Shirai et al. |
| 2005/0289582 A1 | 12/2005 | Tavares et al. |
| 2006/0019224 A1 | 1/2006 | Behar et al. |
| 2006/0143647 A1 | 6/2006 | Bill |
| 2006/0235753 A1 | 10/2006 | Kameyama |
| 2007/0167689 A1 | 7/2007 | Ramadas et al. |
| 2007/0173733 A1 | 7/2007 | Le et al. |
| 2007/0239787 A1 | 10/2007 | Cunningham et al. |
| 2007/0255831 A1 | 11/2007 | Hayashi et al. |
| 2007/0265507 A1 | 11/2007 | de Lemos |
| 2007/0299964 A1 | 12/2007 | Wong et al. |
| 2008/0059570 A1 | 3/2008 | Bill |
| 2008/0091512 A1 | 4/2008 | Marci et al. |
| 2008/0091515 A1 | 4/2008 | Thieberger et al. |
| 2008/0101660 A1 | 5/2008 | Seo |
| 2008/0103784 A1 | 5/2008 | Wong et al. |
| 2008/0184170 A1 | 7/2008 | Periyalwar |
| 2008/0208015 A1 | 8/2008 | Morris et al. |
| 2008/0221472 A1 | 9/2008 | Lee et al. |
| 2008/0287821 A1 | 11/2008 | Jung et al. |
| 2008/0292151 A1* | 11/2008 | Kurtz ............... A61B 3/10 382/128 |
| 2009/0002178 A1 | 1/2009 | Guday et al. |
| 2009/0006206 A1 | 1/2009 | Groe |
| 2009/0083421 A1 | 3/2009 | Glommen et al. |
| 2009/0094286 A1 | 4/2009 | Lee et al. |
| 2009/0112694 A1 | 4/2009 | Jung et al. |
| 2009/0112810 A1 | 4/2009 | Jung et al. |
| 2009/0133048 A1 | 5/2009 | Gibbs et al. |
| 2009/0150919 A1 | 6/2009 | Lee et al. |
| 2009/0156907 A1 | 6/2009 | Jung et al. |
| 2009/0164132 A1 | 6/2009 | Jung et al. |
| 2009/0210290 A1 | 8/2009 | Elliott et al. |
| 2009/0217315 A1 | 8/2009 | Malik et al. |
| 2009/0259518 A1 | 10/2009 | Harvey |
| 2009/0270170 A1 | 10/2009 | Patton |
| 2009/0271417 A1 | 10/2009 | Toebes et al. |
| 2009/0299840 A1 | 12/2009 | Smith |
| 2010/0070523 A1 | 3/2010 | Delgo et al. |
| 2010/0099955 A1 | 4/2010 | Thomas et al. |
| 2010/0266213 A1 | 10/2010 | Hill |
| 2010/0274847 A1 | 10/2010 | Anderson et al. |
| 2010/0324437 A1 | 12/2010 | Freeman |
| 2011/0126226 A1 | 5/2011 | Makhlouf |
| 2011/0134026 A1 | 6/2011 | Kang et al. |
| 2011/0143728 A1 | 6/2011 | Holopainen et al. |
| 2011/0144971 A1 | 6/2011 | Danielson |
| 2011/0196855 A1 | 8/2011 | Wable et al. |
| 2011/0231240 A1 | 9/2011 | Schoen et al. |
| 2011/0251493 A1* | 10/2011 | Poh ............... G06K 9/624 600/477 |
| 2011/0260830 A1 | 10/2011 | Weising |
| 2011/0263946 A1* | 10/2011 | el Kaliouby ......... A61B 5/1128 600/300 |
| 2012/0243751 A1* | 9/2012 | Zheng ............... G06K 9/6255 382/118 |
| 2012/0324491 A1 | 12/2012 | Bathiche et al. |
| 2013/0023337 A1 | 1/2013 | Bowers et al. |
| 2013/0116587 A1 | 5/2013 | Sommo et al. |
| 2013/0197409 A1 | 8/2013 | Baxter et al. |
| 2013/0245462 A1* | 9/2013 | Capdevila ......... A61B 5/02405 600/479 |
| 2014/0172910 A1 | 6/2014 | Jung et al. |
| 2014/0200416 A1* | 7/2014 | Kashef ............ G06F 19/3418 600/301 |
| 2015/0044098 A1* | 2/2015 | Smart ............ A61B 5/0013 422/82.05 |
| 2015/0366456 A1* | 12/2015 | Takamori ............ A61B 5/6898 600/480 |
| 2016/0104486 A1 | 4/2016 | Penilla et al. |
| 2017/0003784 A1 | 1/2017 | Garg et al. |

OTHER PUBLICATIONS

Rana Ayman El Kaliouby, Mind-reading machines: automated inference of complex mental states, Jul. 2005, University of Cambridge, Cambridge, United Kingdom.

International Search Report dated Nov. 14, 2011 for PCT/US2011/39282.

International Search Report dated Apr. 16, 2012 for PCT/US2011/054125.

(56) References Cited

OTHER PUBLICATIONS

International Search Report dated May 24, 2012 for PCT/US2011/060900.

Xiaoyu Wang, An HOG-LBP human detector with partial occlusion handling, Sep. 29, 2009, IEEE 12th International Conference on Computer Vision, Kyoto, Japan.

Zhihong Zeng, A Survey of Affect Recognition Methods: Audio, Visual, and Spontaneous Expressions, Jan. 2009, IEEE Transactions on Pattern Analysis and Machine Intelligence, vol. 31, No. 1.

Nicholas R. Howe and Amanda Ricketson, Improving the Boosted Correlogram, 2004, Lecture Notes in Computer Science, ISSN 0302-9743, Springer-Verlag, Germany.

Xuming He, et al, Learning and Incorporating Top-Down Cues in Image Segmentation, 2006, Lecture Notes in Computer Science, ISBN 978-3-540-33832-1, Springer-Verlag, Germany.

Ross Eaton, et al, Rapid Training of Image Classifiers through Adaptive, Multi-frame Sampling Methods, Oct. 2008, IEEE 37th Applied Imagery Pattern Recognition Workshop, Washington DC.

Verkruysse, Wim, Lars O. Svaasand, and J. Stuart Nelson. "Remote plethysmographic imaging using ambient light." Optics express 16.26 (2008): 21434-21445.

Albiol, Alberto, et al. "Face recognition using HOG—EBGM." Pattern Recognition Letters 29.10 (2008): 1537-1543.

Wu, Hao-Yu, et al. "Eulerian video magnification for revealing subtle changes in the world." (2012). MIT, Cambridge, MA.

* cited by examiner

MENTAL STATE MOOD ANALYSIS USING HEART RATE COLLECTION BASED ON VIDEO IMAGERY

RELATED APPLICATIONS

This application claims the benefit of U.S. provisional patent applications "Deep Convolutional Neural Network Analysis of Images for Mental States" Ser. No. 62/370,421, filed Aug. 3, 2016 and "Image Analysis for Two-Sided Data Hub" Ser. No. 62/469,591, filed Mar. 10, 2017. This application is also a continuation-in-part of U.S. patent application "Mental State Analysis Using Heart Rate Collection Based on Video Imagery" Ser. No. 14/214,719, filed Mar. 15, 2014, which claims the benefit of U.S. provisional patent applications "Mental State Analysis Using Heart Rate Collection Based on Video Imagery" Ser. No. 61/793,761, filed Mar. 15, 2013, "Mental State Analysis Using Blink Rate" Ser. No. 61/789,038, filed Mar. 15, 2013, "Mental State Data Tagging for Data Collected from Multiple Sources" Ser. No. 61/790,461, filed Mar. 15, 2013, "Mental State Well Being Monitoring" Ser. No. 61/798,731, filed Mar. 15, 2013, "Personal Emotional Profile Generation" Ser. No. 61/844,478, filed Jul. 10, 2013, "Heart Rate Variability Evaluation for Mental State Analysis" Ser. No. 61/916,190, filed Dec. 14, 2013, "Mental State Analysis Using an Application Programming Interface" Ser. No. 61/924,252, filed Jan. 7, 2014, and "Mental State Analysis for Norm Generation" Ser. No. 61/927,481, filed Jan. 15, 2014.

The patent application "Mental State Analysis Using Heart Rate Collection Based on Video Imagery" Ser. No. 14/214,719, filed Mar. 15, 2014, is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

This application is also a continuation-in-part of U.S. patent application "Mental State Analysis Using Web Servers" Ser. No. 15/382,087, filed Dec. 17, 2016, which is a continuation in part of "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Data Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The patent application "Mental State Analysis Using Web Servers" Ser. No. 15/382,087, filed Dec. 17, 2016, is also a continuation-in-part of U.S. patent application "Mental State Event Signature Usage" Ser. No. 15/262,197, filed Sep. 12, 2016, which claims the benefit of U.S. provisional patent applications "Mental State Event Signature Usage" Ser. No. 62/217,872, filed Sep. 12, 2015, "Image Analysis In Support of Robotic Manipulation" Ser. No. 62/222,518, filed Sep. 23, 2015, "Analysis of Image Content with Associated Manipulation of Expression Presentation" Ser. No. 62/265,937, filed Dec. 10, 2015, "Image Analysis Using Sub-Sectional Component Evaluation To Augment Classifier Usage" Ser. No. 62/273,896, filed Dec. 31, 2015, "Analytics for Live Streaming Based on Image Analysis within a Shared Digital Environment" Ser. No. 62/301,558, filed Feb. 29, 2016, and "Deep Convolutional Neural Network Analysis of Images for Mental States" Ser. No. 62/370,421, filed Aug. 3, 2016.

The patent application "Mental State Event Signature Usage" Ser. No. 15/262,197, filed Sep. 12, 2016, is also a continuation-in-part of U.S. patent application "Mental State Event Definition Generation" Ser. No. 14/796,419, filed Jul. 10, 2015, which claims the benefit of U.S. provisional patent applications "Mental State Event Definition Generation" Ser. No. 62/023,800, filed Jul. 11, 2014, "Facial Tracking with Classifiers" Ser. No. 62/047,508, filed Sep. 8, 2014, "Semiconductor Based Mental State Analysis" Ser. No. 62/082,579, filed Nov. 20, 2014, and "Viewership Analysis Based On Facial Evaluation" Ser. No. 62/128,974, filed Mar. 5, 2015.

The patent application "Mental State Event Definition Generation" Ser. No. 14/796,419, filed Jul. 10, 2015 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352,166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The patent application "Mental State Event Definition Generation" Ser. No. 14/796,419, filed Jul. 10, 2015 is also a continuation-in-part of U.S. patent application "Mental State Analysis Using an Application Programming Interface" Ser. No. 14/460,915, Aug. 15, 2014, which claims the benefit of U.S. provisional patent applications "Application Programming Interface for Mental State Analysis" Ser. No. 61/867,007, filed Aug. 16, 2013, "Mental State Analysis Using an Application Programming Interface" Ser. No. 61/924,252, filed Jan. 7, 2014, "Heart Rate Variability Evaluation for Mental State Analysis" Ser. No. 61/916,190, filed Dec. 14, 2013, "Mental State Analysis for Norm Generation" Ser. No. 61/927,481, filed Jan. 15, 2014, "Expression Analysis in Response to Mental State Express Request" Ser. No. 61/953,878, filed Mar. 16, 2014, "Background Analysis of Mental State Expressions" Ser. No. 61/972,314, filed Mar. 30, 2014, and "Mental State Event Definition Generation" Ser. No. 62/023,800, filed Jul. 11, 2014.

The patent application "Mental State Analysis Using an Application Programming Interface" Ser. No. 14/460,915, Aug. 15, 2014 is also a continuation-in-part of U.S. patent application "Mental State Analysis Using Web Services" Ser. No. 13/153,745, filed Jun. 6, 2011, which claims the benefit of U.S. provisional patent applications "Mental State Analysis Through Web Based Indexing" Ser. No. 61/352, 166, filed Jun. 7, 2010, "Measuring Affective Data for Web-Enabled Applications" Ser. No. 61/388,002, filed Sep. 30, 2010, "Sharing Affect Across a Social Network" Ser. No. 61/414,451, filed Nov. 17, 2010, "Using Affect Within a Gaming Context" Ser. No. 61/439,913, filed Feb. 6, 2011, "Recommendation and Visualization of Affect Responses to Videos" Ser. No. 61/447,089, filed Feb. 27, 2011, "Video Ranking Based on Affect" Ser. No. 61/447,464, filed Feb. 28, 2011, and "Baseline Face Analysis" Ser. No. 61/467,209, filed Mar. 24, 2011.

The foregoing applications are each hereby incorporated by reference in their entirety.

FIELD OF ART

This application relates generally to analysis of mental states and more particularly to mental state mood analysis using heart rate collection based on video imagery.

BACKGROUND

As all of us have experienced, human emotions or mental states can cause physiological changes depending on the intensity of the emotion. Some emotions can cause physiological changes like sweating, changes in respiration, facial movements, fidgeting, changes to blood pressure, and changes to heart rate. Heart-rate related indications of mental state can include a measure of absolute heart rate (HR), heart rate variability (HRV), and blood volume pulse (BVP). An individual's heart rate can be measured in various ways, including using a medical electrocardiograph (EKG) machine, a chest strap with electrodes, a pulse oximeter that clips on a finger, a sphygmomanometer, or by measuring a pressure point on an individual.

A person's mental state can be impacted by many types of external stimuli. One increasingly common stimulus is interaction with a computer. People spend an ever-increasing amount of time interacting with computers and consume a vast amount of computer-delivered media. This interaction can be for many different reasons, such as desire for educational content, entertainment, social media interaction, document creation, and gaming, to name a few.

In some cases, the human-computer interaction can take the form of a person performing a task using a computer and a software tool running on the computer. Examples of such interactions can include filling out a tax form, creating a document, editing a video, and doing one or more of the other activities that a modern computer can perform. The person might find certain activities interesting or even exciting and might be surprised at how easy it is to perform the activity or activities. The person can become excited, happy, or content as they perform the activities. However, the person might find some activities difficult to perform and can become frustrated or even angry with the computer, even though the computer does not detect emotions. In other cases of human-computer interaction, the person can be consuming content or media such as news, pictures, music, or video, so the detection of a person's mental state can be useful in determining whether or not the person enjoys particular media content.

Currently, tedious methods with limited usefulness are employed to determine users' mental states. For example, users can be surveyed in an attempt to determine their mental state in reaction to a stimulus such as a human-computer interaction. Survey results are often unreliable because the surveys might be completed after the activity was performed, survey participation rates can be low, and people do not often provide accurate and honest answers to the survey questions. In other cases, people can self-rate media to communicate personal preferences by entering a specific number of stars corresponding to a level of like or dislike. However, these types of subjective evaluations are neither a reliable nor practical way to evaluate personal response to media. Recommendations based on such methods are imprecise, subjective, unreliable, and are often further subject to problems related to the small number of individuals willing to participate in the evaluations.

SUMMARY

Heart rate and other types of analyses can be gleaned from facial video as someone observes various media presentations. The information on heart rates can be used to aid in mental state analysis. A method for mental state analysis is described which includes obtaining video of an individual as the individual is interacting with a computer, either by performing various operations or by consuming a media presentation. The video is then analyzed to determine heart rate information on the individual, including both heart rate and heart rate variability. The heart rate information is correlated to a stimulus. A mental state of the individual is then inferred based on the heart rate information. A computer-implemented method for mental state analysis is disclosed comprising: obtaining video of an individual; analyzing the video to determine heart rate information, wherein the analyzing includes: identifying a face of the individual in a portion of the video; separating pixels from the video of the individual, into at least a green pixel temporal intensity trace; training a statistical classifier, wherein the training is learned from a data set consisting of human blood volume pulse synchronized face videos; and recognizing a pulse, from the video of the individual, using the statistical classifier, by learning patterns of variability in the mean of the pixel temporal intensity trace; correlating the heart rate information to a stimulus that the individual is encountering; and inferring, using one or more processors, mental states of the individual based on the heart rate information.

The method includes outputting a mood measurement based on the mental states which were inferred. The method includes analyzing a media presentation based on the mental states which were inferred. The analyzing of the media presentation includes evaluating advertisement effectiveness. The analyzing of the media presentation also includes optimizing the media presentation. The analyzing includes identifying a location of a face of the individual in a portion of the video. The method further includes establishing a region of interest including the face, separating pixels in the region of interest into at least two channel values and combining to form raw traces, transforming and decomposing the raw traces into at least one independent source signal, and processing the at least one independent source signal to obtain the heart rate information. The method includes analyzing an emotional mood of the individual. The method includes enabling the individual to track emotional health. The method includes evaluating a temporal signature for the mental states. The method includes performing unsupervised learning, as part of the training, for pulse recognition.

In embodiments, a computer program product is embodied in a non-transitory computer readable medium, the computer program product comprising code which causes one or more processors to perform operations of: obtaining video of an individual; analyzing the video to determine heart rate information, wherein the analyzing includes: identifying a face of the individual in a portion of the video; separating pixels from the video of the individual, into at least a green pixel temporal intensity trace; training a statistical classifier, wherein the training is learned from a data set consisting of human blood volume pulse synchronized face videos; and recognizing a pulse, from the video of the individual, using the statistical classifier, by learning patterns of variability in the mean of the pixel temporal intensity trace; correlating the heart rate information to a stimulus that the individual is encountering; and inferring mental states of the individual based on the heart rate information. In some embodiments, a computer system for mental state analysis comprises: a memory which stores instructions; one or more processors attached to the memory wherein the one or more processors, when executing the instructions which are stored, are configured to: obtain video of an individual; analyze the video to determine heart rate information, wherein analyzing includes: identifying a face of the individual in a portion of the video; separating pixels from the video of the individual into at least a green pixel temporal intensity trace; training a statistical classifier, wherein the training is learned from a data set consisting of human blood volume pulse synchronized face videos; and recognizing a pulse, from the video of the individual, using the statistical classifier, by learning patterns of variability in the mean of the pixel temporal intensity trace; correlate the heart rate information to a stimulus that the individual is encountering; and infer mental states of the individual based on the heart rate information.

Various features, aspects, and advantages of various embodiments will become more apparent from the following further description.

BRIEF DESCRIPTION OF THE DRAWINGS

The following detailed description of certain embodiments may be understood by reference to the following figures wherein.

DETAILED DESCRIPTION

Figure 1:
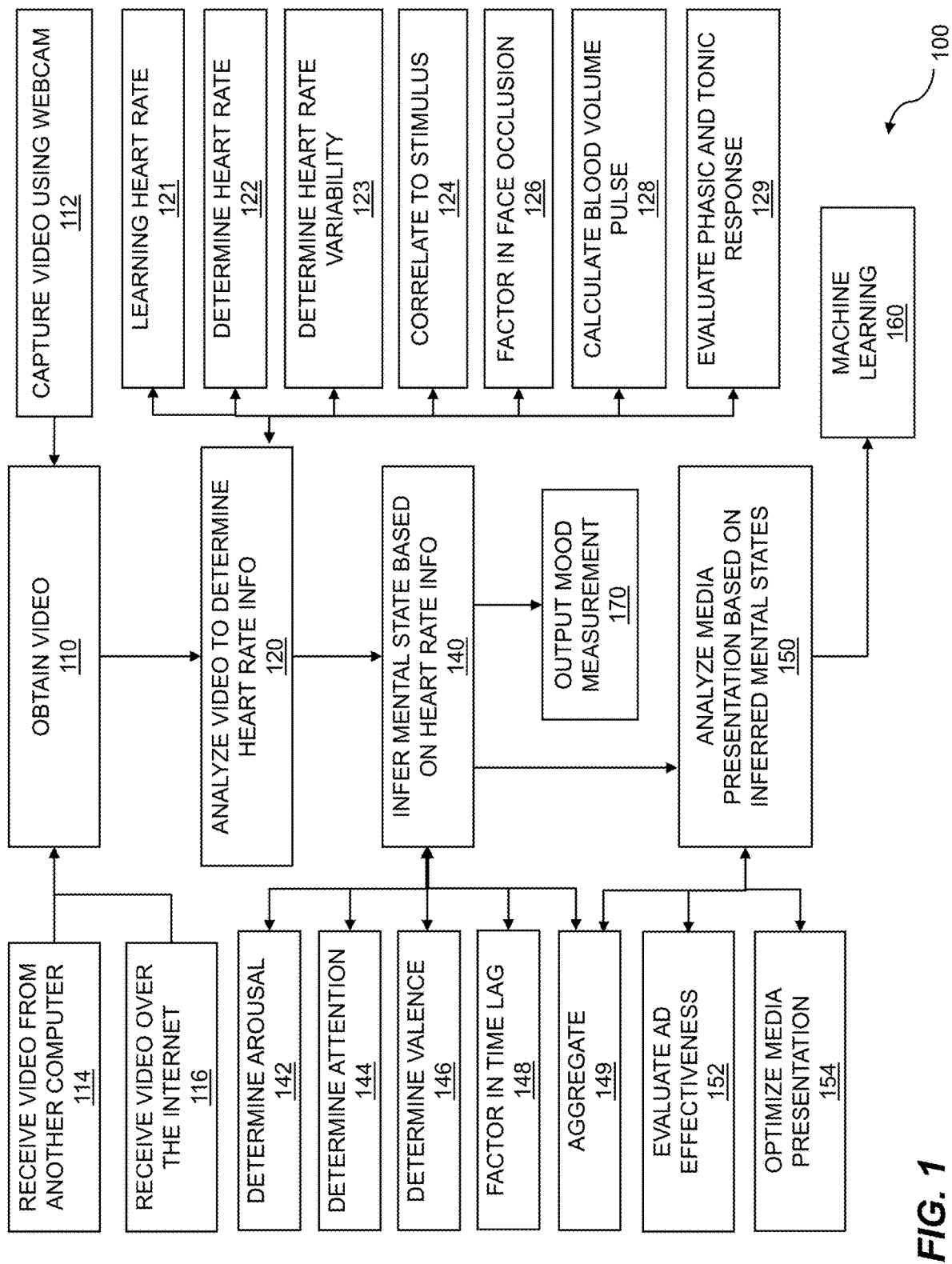
FIG. 1 is a flow diagram for mental state analysis.

As an individual interacts with a computer, the individual's mental state can be impacted by the interaction. This might affect the individual's facial expressions and heart rate, as well as provoke other physiological reactions. Determining the individual's mental state can have value for a variety of reasons, such as improving the program that the individual is using, rating a media presentation, or optimizing an advertisement. Traditional methods of monitoring an individual's mental state have limited effectiveness. For example, surveys or rating systems are prone to non-participation and inaccurate reporting, and while physiological information is often an accurate way to determine an individual's mental state, traditional physiological monitoring devices are intrusive and not available at most computer workstations.

Many contemporary computer systems already include a webcam, and even for systems without a webcam, it is possible to easily and inexpensively add one to nearly any modern computer workstation. In many cases, a webcam can unobtrusively monitor an individual, but until recently it was not known how to determine heart rate information from a video produced by a webcam. Recent studies have shown, however, that it is possible to extract heart rate information from video of an individual. Examples of such work include "Remote plethysmographic imaging using ambient light" by Wim Verkruysse, Lars O Svaasand, and J Stuart Nelson, published in Optics Express, Vol. 16, No. 26, on Dec. 12, 2008, and U.S. patent application publication US 2011/0251493 A1, published on Oct. 31, 2011, entitled "Method and System for Measurement of Physiological Parameters;" with Ming-Zher Poh, Daniel McDuff, and Rosalind Picard as named inventors. These papers are hereby incorporated by reference in their entirety. The present disclosure describes using a video of an individual to determine heart rate information and then using the heart rate information to infer a mental state of that individual.

An individual can interact with a computer to perform some type of task on the computer or view a media presentation while being monitored by a webcam. The video from the webcam can then be analyzed to determine heart rate information. In one embodiment, the video is separated into separate color channels and a trace is generated for each color channel based on the spatial average of the color channel for the face over time. Independent component analysis can then be used to generate independent source signals that correlate to heart rate information, such as blood volume pulse (BVP). Signal processing techniques can then be used to extract heart rate information, including heart rate variability, arrhythmias, heart murmurs, beat strength and shape, artery health, or arterial obstructions. In some embodiments, respiration rate information is also determined.

Once the heart rate information has been determined, a mental state of the individual can be inferred. Mental states which can be inferred include frustration, confusion, disappointment, hesitation, cognitive overload, focusing, engagement, attention, boredom, exploration, confidence, trust, delight, disgust, skepticism, doubt, satisfaction, excitement, laughter, calmness, happiness, sadness, anger, stress, sentimentality, or curiosity. Various types of heart rate information can be used to infer a mental state. For example, an elevated HR can indicate excitement, a decrease in phasic HR can indicate attention, and tonic HR can be used to indicate arousal. In some embodiments, the heart rate information is used in conjunction with facial movement data and/or other biosensor data to infer a mental state.

FIG. 1 is a flow diagram for mental state analysis. The flow 100 describes a computer-implemented method for mental state analysis. The flow 100 includes obtaining video 110 of an individual. In some embodiments, the video is captured using a webcam 112, while in other embodiments, the video is received from another computer 114 and/or over the Internet 116. The video can be color video and can be of various spatial resolutions, frame rates (temporal resolution), and lengths. In some embodiments, a video clip of at least one to three seconds of video is obtained, but in other embodiments, a video clip of 20 seconds or more is obtained. In some embodiments, video is continuously captured, while in other embodiments, video is broken into segments, such as 20-second segments, for analysis. Some embodiments continuously analyze the video. In some embodiments, the video is a standard resolution television-type video at resolutions such as 720×540, 720×480 or 640×480 pixels with a frame rate of 25 or 30 frames per second (FPS) interlaced or progressive. In other embodiments, the video is a high-definition video at resolutions such as 1280×720 pixels progressive or 1920×1080 interlaced with a frame rate of 30 to about 60 FPS. But, in some embodiments, the video is at a lower spatial and/or temporal resolution as is commonly captured by an inexpensive webcam, such as CIF (352×240), QCIF (176×120), or another video type at a lower resolution and with a frame rate of 25 FPS or lower, such as 15 FPS, for example. In some embodiments, the video includes a series of images of the individual, and the video has a variable frame rate. In some embodiments, a specialty camera capable of capturing high frame rate video, such as video with a frame rate faster than 60 FPS, is used. Some embodiments include video processed at 0.1 (FPS) and above, frame sizes of 1 pixel and above, and even image sequences at irregular temporal sampling and spatial sizes. In embodiments, the method includes converting the video to a constant frame rate and performing filtering on the video to facilitate the analyzing.

The flow 100 continues by analyzing the video to determine heart rate information 120. The analyzing can be performed using any type of algorithm, but one algorithm that can be used is described in more detail in FIG. 3. In some embodiments, the analyzing the video includes learning about heart rate information 121. In some embodiments, the heart rate information includes a measure of heart rate (HR) 122. The heart rate can be an instantaneous heart rate or an average heart rate over a period of time. In some embodiments, the heart rate information includes heart rate variability (HRV) 123. In some embodiments, the analyzing correlates the heart rate information to a stimulus 124 such as a scene of a movie, a portion of an advertisement, a specific task performed within a software application, or any other type of stimulus generated by the individual's interaction with the computer, by an external event, or through some other context. The context can include viewing a concept, viewing a product, and interacting with a person or persons. In some cases, a wearable apparatus can view and record another person's face. The video from that person's face can then be analyzed for heart rate information. In some embodiments, two or more people each have a wearable apparatus, and video information is collected, analyzed, and exchanged among the people or provided to another system for utilization. The analyzing can factor in a facial occlusion 126 for part of an individual's face. This is accomplished, in some embodiments, by recognizing that the face is occluded and adjusting a region of interest for the frames where the face is partially occluded, along with removing the frames where more than a predetermined portion of the face is occluded. In some embodiments, the analyzing includes calculating blood volume pulse (BVP) 128. The BVP can be included in the heart rate information and/or can be used to calculate the heart rate information, depending on the embodiment.

The analyzing can include evaluating phasic and/or tonic response 129 of the heart rate information. A phasic response is a short-term, or high-frequency, response to a stimulus, and a tonic response is a long-term, or low-frequency, response to a stimulus. In one embodiment, a phasic response constitutes a heartbeat-to-heartbeat difference, while in other embodiments, a phasic response constitutes a difference over some number of seconds, such as a period between about two and about 10 seconds. Other embodiments use a different threshold for a phasic response. A tonic response can represent a change over a longer period of time, such as a change observed during any period of time from 10 seconds to many minutes or longer. HR, HRV, and BVP can all have both phasic and tonic responses. In addition, analyzing can include extracting a heart rate from evaluation of a face of the individual in the video, and the heart rate can be an equivalent to a blood volume pulse value. The analyzing can use a green channel from the video.

The flow 100 further comprises inferring an individual's mental states based on the heart rate information 140. The mental states can include one or more of frustration, confusion, disappointment, hesitation, cognitive overload, focusing, engagement, attention, boredom, exploration, confidence, trust, delight, disgust, skepticism, doubt, satisfaction, excitement, laughter, calmness, stress, and curiosity. The inferring can include determining arousal 142, determining attention 144, and/or determining valence 146. The method can include interpreting physiological arousal from the heart rate information. Various combinations of the absolute value, relative value, phasic response, and/or tonic response of HR, HRV, BVP, and/or other heart rate information can be used for the inferring. For example, a phasic response of HR can be used to infer attention and a tonic response of HR can be used to infer arousal. A decrease in phasic HR can be used to infer a change of valence with a measure of tonic HR used to infer the direction of the change of valence. In some embodiments, a time lag is factored into the inference 148, as there can be a lag between the video and the stimulus as well as a lag in the individual's heart-rate response to the stimulus. The time-lag factoring can be used to help correlate the response to a specific stimulus. In some embodiments, the flow 100 further comprises aggregating 149 the heart rate information for the individual with other people and/or inferring mental states of a plurality of other people based on the heart rate information on the plurality of other people. Such aggregation can be useful in determining a mental state of the group of people, or a group's response to a certain stimulus.

The flow 100 further comprises analyzing a media presentation based on the mental states which were inferred 150. The media presentation can be any type of media presentation, but can include one or more of an advertisement, a movie, a television show, a web series, a webisode, a video, a video clip, an electronic game, a concept presentation, an e-book, an e-magazine, or an app. Some embodiments further comprise aggregating 149 the mental states for the individual with other people. The analyzing can include comparing the mental state to an intended mental state to determine if the media presentation is effective. So, if the media presentation is an advertisement, the analyzing of the media presentation can include evaluating advertisement effectiveness 152. In some embodiments, different versions of the media presentation are presented and the mental states of the individual or the group are compared for the different versions. The media presentation is changed, in some embodiments, based on the mental states. Such changes can include changing a length of the media presentation, adding or deleting scenes, or choosing appropriate music for the soundtrack, among others. Thus, the analyzing of the media presentation can include optimizing the media presentation 154. The flow 100 can further include learning 160 about heart rate information as part of the analyzing the media presentation. The learning can factor in one or more previous frames of data and can apply transformations, either previously learned or learned on the fly, to the traces for this analysis to promote the capture of heart rate signal fluctuations in the video due to blood flow. One or more previous frames can be used as training data for an individual, for people with similar skin pigmentation, or for people in general. The learning can occur on-the-fly or can be stored for future use with a certain individual or group of people. The learning can be used for global independent component analysis and/or other transformations. Further, a set of videos can be processed in order to learn heart rate information analysis. In some embodiments, unsupervised learning is performed as part of the training for pulse recognition. In some embodiments, image descriptors are learned as part of the training for emotional content.

The flow 100 includes outputting a mood measurement 170 based on the mental states that were inferred. The mood measurement can reflect a single mental state or reflect a composite of several mental states, along with the temporal timing, length, and strength of the several mental states. For example, an inferred mental state of attentiveness might result in outputting a mood of being satisfied, whereas an inferred mental state of attentiveness along with increased arousal and positive valence might result in outputting a mood of being happy. Temporal signatures for the mental states can be evaluated. A temporal signature is a representation of one or more elements, such as mental states, according to their occurrence in the time domain. For example, a happy scene in a movie that suddenly turns scary would produce a temporal signature of those mental states that represents the emotional content of an individual's response to a stimulus. Detecting certain temporal signatures in certain sequences can then be used to infer additional mental states.

The flow 100 can further comprise collecting facial data based on the video. The facial data can include facial movements, which, in at least some embodiments, is categorized using the facial action coding system (FACS). The inferring of mental states can be based, at least in part, on the facial data; thus the facial data can be used in combination with the heart rate information for the inferring of mental states. Various steps in the flow 100 may be changed in order, repeated, omitted, or the like without departing from the disclosed concepts. Various embodiments of the flow 100 may be included in a computer program product embodied in a non-transitory computer readable medium that includes code executable by one or more processors.

Figure 2:
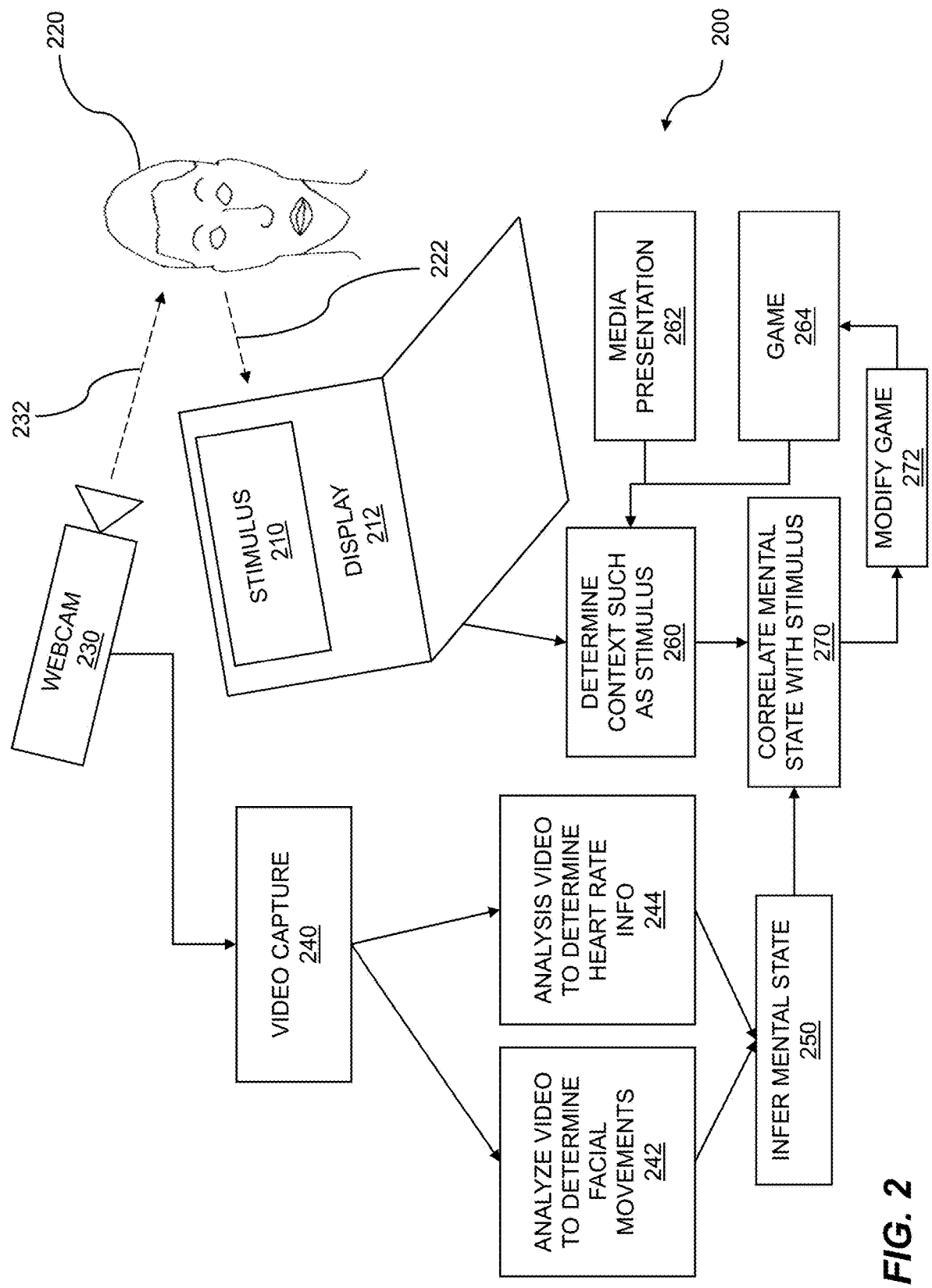
FIG. 2 is a flow diagram for video capture and analysis.

FIG. 2 is a flow diagram 200 for video capture and analysis. An individual 220 can view 222 an electronic display 212 showing a stimulus 210 to the individual 220. The electronic display 212 can be a part of, or can be driven from, a device capturing a video of the individual, or the electronic display can only be loosely coupled or even unrelated to the device capturing the video, depending on the embodiment. The video is captured, in some embodiments, using a mobile device such as a cell phone, a tablet computer, a wearable computing device, or a laptop. The capturing can also be performed with a webcam 230. Thus the obtaining the video of the individual comprises capturing the video with a webcam 230, in some embodiments.

The webcam 230 can have a line-of-sight 232 to the user's face 220, and can capture any one or more of video, audio, and still images of the individual 220. A webcam, as the term is used herein, can include a video camera, a still camera, a thermal imager, a CCD device, a phone camera, a three-dimensional camera, a depth camera, multiple webcams used to show different views of a person, or any other type of image capture apparatus which can allow image data to be captured and used in an electronic system. The images of the person 220 as taken by the webcam 230 can be captured by a video capture unit 240. In some embodiments, video is captured, while in others, one or more still images are captured at regular or irregular intervals. In some embodiments, the one or more still images are used to create a video, which can have a variable frame rate. The captured video or still images can be analyzed to determine one or both of facial movements 242 and heart rate information 244. The facial movements can include information on facial expressions, action units, head gestures, smiles, smirks, brow furrows, squints, lowered eyebrows, raised eyebrows, or attention. In some embodiments, the webcam 230 also captures images of the setting, which can assist in determining contextual information, other physiological data, gestures, actions, and/or other movements. The analysis of the video can be used to infer a mental state 250 of the user 220.

The flow 200 can further comprise determining contextual information 260, such as identifying the stimulus 210. In some embodiments, the contextual information includes other information, such as other individuals nearby whose images can be captured by the webcam 230, environmental information, identity information about the user 220, or another type of contextual information. The electronic display 212 can include a stimulus 210 such as a media presentation or the user interface of a computer program. Thus, the stimulus 210 can pertain to a media presentation 262. The media presentation 262 can include one of a group consisting of a movie, a television show, a web series, a webisode, a video, a video clip, an electronic game, an e-book, or an e-magazine. In other embodiments, the stimulus 210 is based on a game device 264, appliance, vehicle, sensor, application, robot, or system with which the user 220 is interacting using the display 212.

The heart rate information can be correlated 270 to a stimulus that the individual is encountering, and, in at least some embodiments, the inferring factors in the time lag between a stimulus 210 and the heart rate information. This can allow conclusions to be formed about the interaction of the user 220 with the stimulus 210. In some embodiments, the media presentation 262 is optimized based on the correlation of the mental state to the stimulus. In some embodiments, a game 264 is changed in some way based on the mental state inferred from the heart rate information and/or the facial movements. Thus, the game 264 can be modified 272 based on the heart rate information. The game can be modified in many different ways. For example, the game's difficulty can be changed, or a player's avatar can be modified to match, modify, or disguise the player's mental state by adjusting the avatar's facial expressions or body actions. That is, in embodiments, the avatar performs an action such as smiling or frowning based on the user's mental state.

Figure 3:
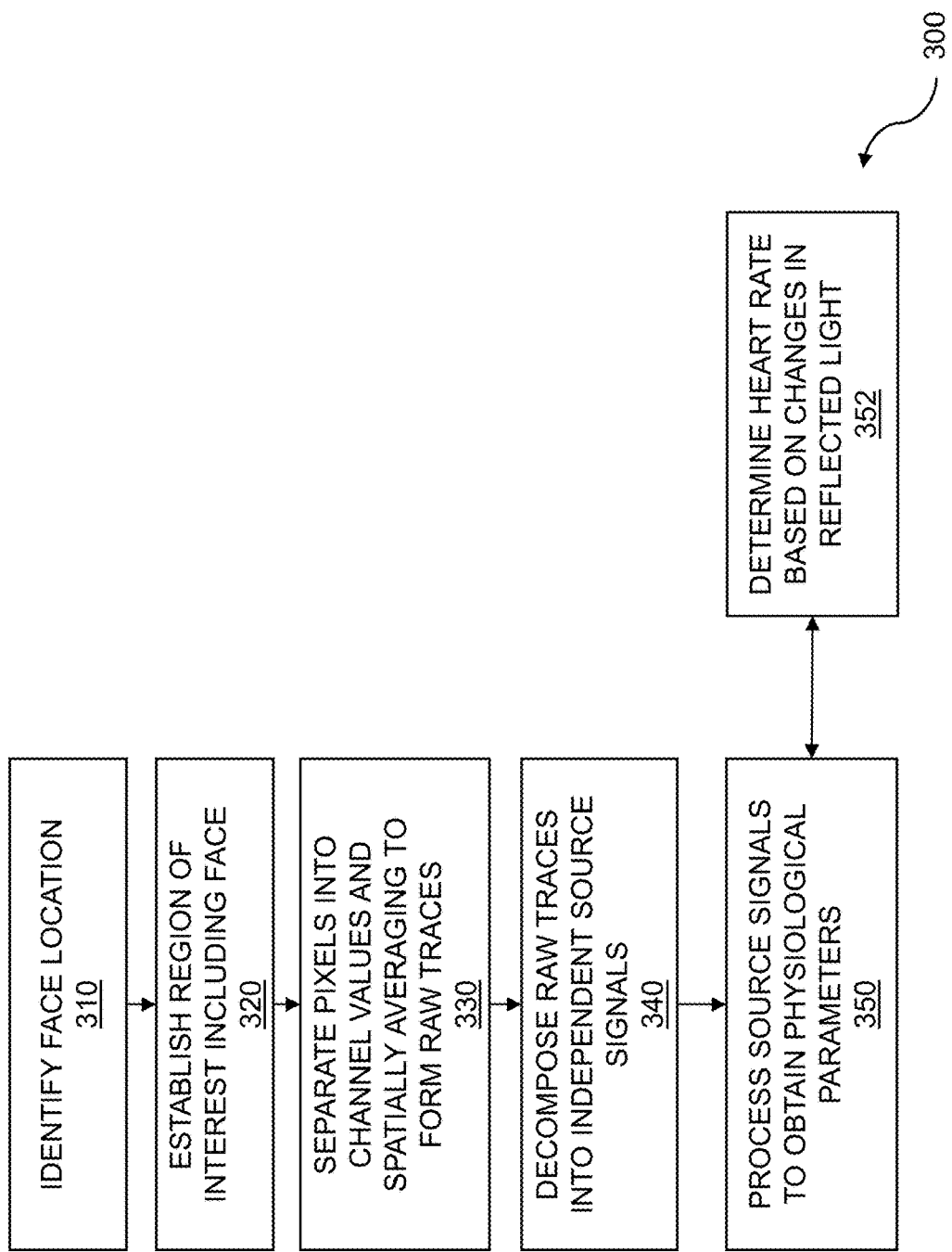
FIG. 3 is a flow diagram for determining heart rate information by analyzing video.

FIG. 3 is a flow diagram for determining heart rate information by analyzing video. While the embodiment described in flow 300 has been shown to provide accurate heart rate information from a video, other embodiments use different algorithms for determining heart rate information by analyzing video. In this embodiment, the analyzing includes identifying a location of a face 310, or a set of faces, of an individual, or multiple individuals, in a portion of a video. Facial detection can be performed using a facial landmark tracker. The tracker can identify points on a face and can be used to localize sub-facial parts such as the forehead and/or cheeks. Further, skin detection can be performed and facial portions removed from images where those portions are considered irrelevant. In some cases, eyes, lips, or other portions can be ignored within images. The flow 300 further comprises establishing a region of interest (ROI) including the face 320. In at least one embodiment, the ROI is defined as a portion of a box returned as the location of the face, such as the middle sixty-percent of the width of the box and the full height of the box, for example. In another embodiment, the ROI is obtained via skin-tone detection and is determined using various regions of skin on an individual's body, including non-facial regions. In some embodiments, the ROI is processed using various image-processing techniques including, but not limited to, sharpness filters, noise filters, convolutions, and brightness and/or contrast normalization that can operate on a single frame or a group of frames over time. The flow 300 can scale its analysis to process multiple faces within multiple regions of interests (ROI) returned by the facial landmark detector.

The flow 300 can further comprise separating temporal pixel intensity traces in the regions of interest into at least two channel values and spatially and/or temporally processing the separated pixels to form raw traces 330. While one embodiment establishes red, green, and blue as channel values, other embodiments base channels on another color gamut, or other functions of the pixel intensity traces. The channels of the video can be analyzed on a frame-by-frame basis and spatially averaged to provide a single value for each frame in each channel. Some embodiments use a weighted average to emphasize certain areas of the face. One raw trace per channel can be created and can include a single value that varies over time. In some embodiments, the raw traces are processed for filtering or enhancement. Such processing can include various filters such as low-pass, high-pass, or band-pass filters; interpolation; decimation; or other signal processing techniques. In at least one embodiment, the raw traces are detrended using a procedure based on a smoothness priors approach. Other types of analysis are alternatively possible, such as a feature being extracted from a channel based on a discrete probability distribution of pixel intensities. A histogram of intensities can be generated with a histogram per channel. In some embodiments, one bin is considered equivalent to summing spatially. Analysis can include tracing fluctuations in reflected light from the skin of a person being viewed.

The flow 300 can further comprise decomposing the raw traces into at least one independent source signal 340. The decomposition can be accomplished using independent component analysis (ICA). Independent component analysis (ICA) is a technique for uncovering independent signals from a set of observations composed of linear mixtures of underlying sources. In this case, the underlying source signal of interest can be BVP. During the cardiac cycle, volumetric changes in the blood vessels modify the path length of the incident ambient light, which in turn changes the amount of light reflected, a measurement which can indicate the timing of cardiovascular events. By capturing a sequence of images of the facial region with a webcam, the red, green, and blue (RGB) color sensors pick up a mixture of reflected plethysmographic signals along with other sources of fluctuations in light due to artifacts. Given that hemoglobin absorptivity differs across the visible and near-infrared spectral range, each color sensor records a mixture of the original source signals with slightly different weights. The ICA model assumes that the observed signals are linear mixtures of the sources where one of the sources is hemoglobin absorptivity or reflectivity. ICA can be used to decompose the raw traces into a source signal representing hemoglobin absorptivity correlating to BVP. Respiration rate information is also determined, in some embodiments.

The flow 300 further comprises processing at least one source signal to obtain the heart rate information 350. Heart rate (HR) can be determined by observing the intervals between peaks of the source signal, finding the peaks having been discussed above. Thus, the heart rate information can include heart rate, and the heart rate can be determined based on changes in the amount of reflected light 352. Heart rate variability, both phasic and tonic, can be obtained using a power spectral density (PSD) estimation and/or through other signal processing techniques. The analysis can include evaluation of phasic and tonic heart rate responses. In some embodiments, the video includes a plurality of other people. Such embodiments can comprise identifying locations for faces of the plurality of other people and analyzing the video to determine heart rate information on the plurality of other people. Inferring mental states of the plurality of other people based on the heart rate information on the plurality of other people can be included. Various steps in the flow 300 may be changed in order, repeated, omitted, or the like without departing from the disclosed concepts. Various embodiments of the flow 300 may be included in a computer program product embodied in a non-transitory computer readable medium that includes code executable by one or more processors.

In other embodiments, a supervised learning approach is adopted to the problem of detecting human heart rate. A statistical classifier can be trained by learning from a data set consisting of human blood volume pulse synchronized with face videos. The classifier will recognize a pulse by learning patterns of variability, in the mean of the green channel, that correspond to a beat in the blood volume pulse values. After training, the classifier can process a sequence of frames and thereby report a heartbeat when it detects a pattern in the green channel similar to the pattern seen during training. The classifier can return a number that could be positive or negative. A larger number is returned as a result of a higher confidence by the classifier. In some embodiments, progressive filtering is used to enable shorter time spans in the heart rate analysis. In some cases, each beat can be evaluated for a heart rate. In embodiments, facial images are compensated for media images that are reflected from the face due to screen lighting.

Figure 4:
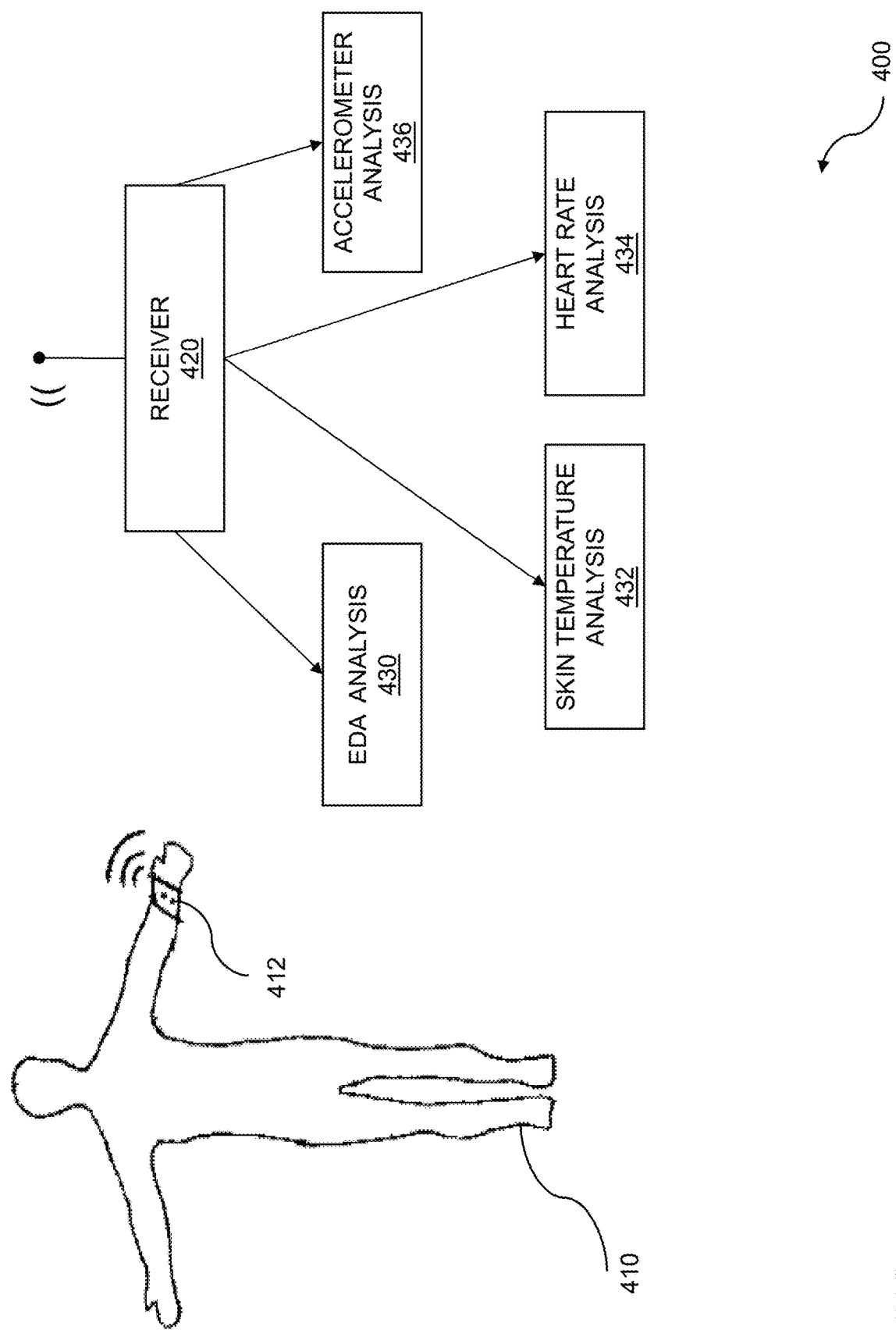
FIG. 4 is a diagram showing sensor analysis.

FIG. 4 is a diagram showing sensor analysis. The diagram 400 comprises obtaining biosensor data for the individual 410. Data can be collected from a person 410 as he or she interacts with a computer or views a media presentation. The person 410 can have a biosensor 412 attached to him or her for the purpose of collecting mental state data. The biosensor 412 can be placed on the wrist, palm, hand, head, or another part of the body. In some embodiments, multiple biosensors are placed on the body in multiple locations. The biosensor 412 can include detectors for physiological data such as electrodermal activity, skin temperature, accelerometer readings, respiration, and the like. Other detectors for physiological data can also be included, such as heart rate, heart rate variability, blood pressure, EKG, EEG, other types of brain waves, and other physiological detectors. The biosensor 412 can transmit collected information to a receiver 420 using wireless technology such as Wi-Fi, Bluetooth, 802.11, cellular, or other protocols. In other embodiments, the biosensor 412 communicates with the receiver 420 using other methods, such as a wired or optical interface. The receiver can provide the data to one or more components in the system 400. In some embodiments, the biosensor 412 records multiple types of physiological information in memory for later download and analysis. In some embodiments, the download of recorded physiological data is accomplished through a USB port or another form of wired or wireless connection. The biosensor data can augment the heart rate information determined by analyzing video of the person 410.

Mental states can be inferred based on physiological data, including physiological data from the sensor 412 which can be used to augment the heart rate information determined by analyzing video. Mental states can also be inferred, at least in part, based on facial expressions and head gestures observed by a webcam, or based on a combination of data from the webcam and data from the sensor 412. The mental states can be analyzed based on arousal and valence. Arousal can range from being highly activated, such as when someone is agitated, to being entirely passive, such as when someone is bored. Valence can range from being very positive, such as when someone is happy, to being very negative, such as when someone is angry. Physiological data can include one or more of electrodermal activity (EDA), heart rate, heart rate variability, skin temperature, respiration, accelerometer readings, and other types of analysis of a human being. It will be understood that both here and elsewhere in this document, physiological information can be obtained either by the biosensor 412 or by facial observation via an image capturing device. Facial data can include facial actions and head gestures used to infer mental states. Further, the data can include information on hand gestures or body language and body movements such as visible fidgets. In some embodiments, these movements are captured by cameras, while in other embodiments these movements are captured by sensors. Facial data can include the tilting of the head to the side, leaning forward, smiling, and frowning, among numerous other gestures or expressions.

In some embodiments, electrodermal activity is collected continuously, periodically, or sporadically. The electrodermal activity can be analyzed 430 to indicate arousal, excitement, boredom, or other mental states based on observed changes in skin conductance. Skin temperature can be collected and recorded. In turn, the skin temperature can be analyzed 432. Changes in skin temperature can indicate arousal, excitement, boredom, or other mental states. Heart rate can be collected and recorded and can also be analyzed 434. A high heart rate can indicate excitement, arousal, or other mental states. Accelerometer data can be collected and used to track one, two, or three dimensions of motion. The accelerometer data can be recorded. The accelerometer data can be analyzed 436 and can indicate a sleep pattern, a state of high activity, a state of lethargy, or other states. The various data collected by the biosensor 412 can be used along with the heart rate information determined by analyzing video captured by the webcam in the analysis of mental state.

Figure 5:
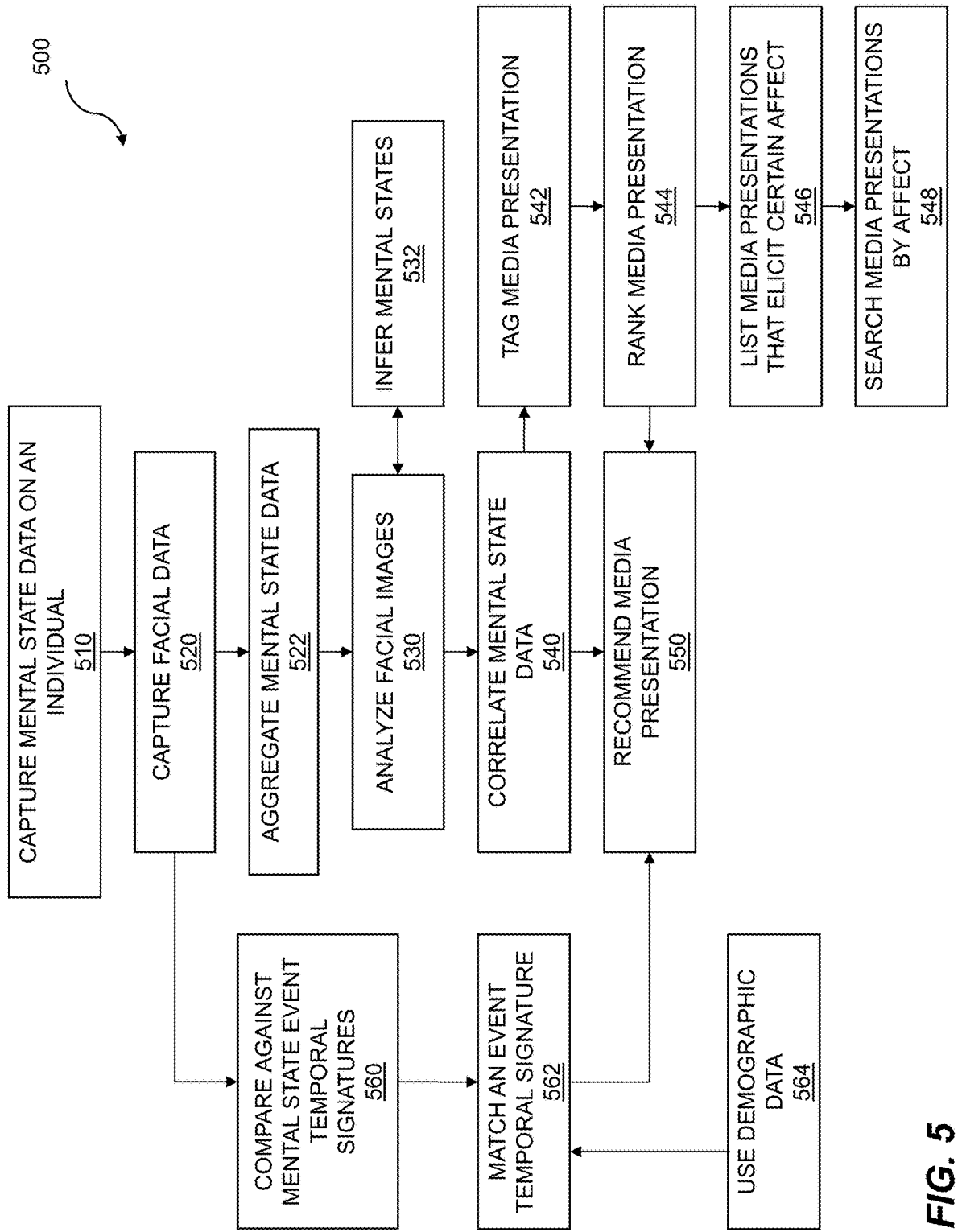
FIG. 5 is a flow diagram for mental state-based recommendations.

FIG. 5 is a flow diagram for mental state-based recommendations and shows a flow 500 which describes a computer-implemented method for mental state-based stimuli analysis. The flow 500 begins with capturing mental state data on an individual 510. The capturing can be based on displaying stimuli to an individual or a group of people of which the individual is a part. The displaying can be done all at once or through multiple occurrences. The plurality of media presentations can include videos. The plurality of videos can include YouTube™ videos, Vimeo™ videos, or Netflix™ videos. Further, the plurality of media presentations can include a movie, a movie trailer, a television show, a web series, a webisode, a video, a video clip, an advertisement, a music video, an electronic game, an e-book, or an e-magazine. The flow 500 continues with capturing facial data 520. The facial data can identify a first face. The captured facial data can be from the individual or from the group of people of which the individual is a part while the plurality of media presentations is displayed. Thus, mental state data can be captured from multiple people. The mental state data can include facial images. In some embodiments, the playing of the media presentations is done on a mobile device and the recording of the facial images is done with the mobile device. The flow 500 includes aggregating the mental state data 522 from the multiple people. The flow 500 further comprises analyzing the facial images 530 for a facial expression. The facial expression can include a smile or a brow furrow. The flow 500 can further comprise using the facial images to infer mental states 532. The mental states can include frustration, confusion, disappointment, hesitation, cognitive overload, focusing, being engaged, attending, boredom, exploration, confidence, trust, delight, valence, skepticism, satisfaction, and the like.

The flow 500 includes correlating the mental state data 540 captured from the group of people who have viewed the plurality of media presentations and had their mental state data captured. The plurality of videos viewed by the group of people can have some common videos seen by each of the people in the group of people. In some embodiments, the plurality of videos does not include an identical set of videos. The flow 500 can continue with tagging the plurality of media presentations 542 with mental state information based on the mental state data which was captured. In some embodiments, the mental state information is simply the mental state data, while in other embodiments, the mental state information is the inferred mental states. In still other embodiments, the mental state information is the result of the correlation. The flow 500 can continue with ranking the media presentations 544 relative to another media presentation based on the mental state data which was collected. The ranking can be for an individual based on the mental state data captured from the individual. The ranking can be based on anticipated preferences for the individual. In some embodiments, the ranking of a first media presentation relative to another media presentation is based on the mental state data which was aggregated from multiple people. The ranking can also be relative to media presentations previously stored with mental state information. The ranking can include ranking a video relative to another video based on the mental state data which was captured. The flow 500 can further comprise displaying the videos which elicit a certain mental state 546. The certain mental states can include smiles, engagement, attention, interest, sadness, liking, disliking, and so on. The ranking can further comprise displaying the videos which elicited a larger number of smiles. As a result of ranking, the media presentations can be sorted based on which videos are the funniest, the saddest, which generate the most tears, or which engender some other response. The flow 500 can further comprise searching through the videos based on a certain mental state data 548. A search 548 can identify videos which are very engaging, funny, sad, poignant, or the like.

The flow 500 includes comparing the mental state data that was captured for the individual against a plurality of mental state event temporal signatures 560. In embodiments, multiple mental state event temporal signatures have been obtained from previous analysis of numerous people. The mental state event temporal signatures can include information on rise time to facial expression intensity, fall time from facial expression intensity, duration of a facial expression, and so on. In some embodiments, the mental state event temporal signatures are associated with certain demographics, ethnicities, cultures, etc. The mental state event temporal signatures can be used to identify one or more of sadness, stress, happiness, anger, frustration, confusion, disappointment, hesitation, cognitive overload, focusing, engagement, attention, boredom, exploration, confidence, trust, delight, disgust, skepticism, doubt, satisfaction, excitement, laughter, calmness, curiosity, humor, depression, envy, sympathy, embarrassment, poignancy, or mirth. The mental state event temporal signatures can be used to identify liking or satisfaction with a media presentation. The mental state event temporal signatures can be used to correlate with appreciating a second media presentation. The flow 500 can include matching a first event signature 562, from the plurality of mental state event temporal signatures, against the mental state data that was captured. In embodiments, an output rendering is based on the matching of the first event signature. The matching can include identifying similar aspects of the mental state event temporal signature such as rise time, fall time, duration, and so on. The matching can include matching a series of facial expressions described in mental state event temporal signatures. In some embodiments, a second mental state event temporal signature is used to identify a sequence of mental state data being expressed by an individual. In some embodiments, demographic data 564 is used to provide a demographic basis for analyzing temporal signatures.

The flow 500 includes recommending a second media presentation 550 to an individual based on the mental state data that was captured and based on the ranking. The recommending the second media presentation to the individual is further based on the comparing of the mental state data to the plurality of mental state event temporal signatures. The second media presentation can be a movie, a movie trailer, a television show, a web series, a webisode, a video, a video clip, an advertisement, a music video, an electronic game, an e-book, or an e-magazine. The recommending the second media presentation can be further based on the matching of the first event signature. The recommending can be based on similarity of mental states expressed. The recommending can be based on a numerically quantifiable determination of satisfaction or appreciation of the first media and an anticipated numerically quantifiable satisfaction or appreciation of second first media presentation.

Based on the mental states, recommendations to or from an individual can be provided. One or more recommendations can be made to the individual based on mental states, affect, or facial expressions. A correlation can be made between one individual and others with similar affect exhibited during multiple videos. The correlation can include a record of other videos, games, or other experiences, along with their affect. Likewise, a recommendation for a movie, video, video clip, webisode or another activity can be made to an individual based on their affect. Various steps in the flow 500 may be changed in order, repeated, omitted, or the like without departing from the disclosed inventive concepts. Various embodiments of the flow 500 may be included in a computer program product embodied in a non-transitory computer readable medium that includes code executable by one or more processors.

The human face provides a powerful communications medium through its ability to exhibit a myriad of expressions that can be captured and analyzed for a variety of purposes. In some cases, media producers are acutely interested in evaluating the effectiveness of message delivery by video media. Such video media includes advertisements, political messages, educational materials, television programs, movies, government service announcements, etc. Automated facial analysis can be performed on one or more video frames containing a face in order to detect facial action. Based on the facial action detected, a variety of parameters can be determined including affect valence, spontaneous reactions, facial action units, and so on. The parameters that are determined can be used to infer or predict emotional and mental states. For example, determined valence can be used to describe the emotional reaction of a viewer to a video media presentation or another type of presentation. Positive valence provides evidence that a viewer is experiencing a favorable emotional response to the video media presentation, while negative valence provides evidence that a viewer is experiencing an unfavorable emotional response to the video media presentation. Other facial data analysis can include the determination of discrete emotional states of the viewer or viewers.

Facial data can be collected from a plurality of people using any of a variety of cameras. A camera can include a webcam, a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. In some embodiments, the person is permitted to "opt-in" to the facial data collection. For example, the person can agree to the capture of facial data using a personal device such as a mobile device or another electronic device by selecting an opt-in choice. Opting-in can then turn on the person's webcam-enabled device and can begin the capture of the person's facial data via a video feed from the webcam or other camera. The video data that is collected can include one or more persons experiencing an event. The one or more persons can be sharing a personal electronic device or can each be using one or more devices for video capture. The videos that are collected can be collected using a web-based framework. The web-based framework can be used to display the video media presentation or event as well as to collect videos from any number of viewers who are online. That is, the collection of videos can be crowdsourced from those viewers who elected to opt-in to the video data collection.

In some embodiments, a high frame rate camera is used. A high frame rate camera has a frame rate of sixty frames per second or higher. With such a frame rate, micro expressions can also be captured. Micro expressions are very brief facial expressions, lasting only a fraction of a second. They occur when a person either deliberately or unconsciously conceals a feeling.

In some cases, micro expressions happen when people have hidden their feelings from themselves (repression) or when they deliberately try to conceal their feelings from others. Sometimes the micro expressions might only last about fifty milliseconds. Hence, these expressions can go unnoticed by a human observer. However, a high frame rate camera can be used to capture footage at a sufficient frame rate such that the footage can be analyzed for the presence of micro expressions. Micro expressions can be analyzed via action units as previously described, with various attributes such as brow raising, brow furls, eyelid raising, and the like. Thus, embodiments analyze micro expressions that are easily missed by human observers due to their transient nature.

The videos captured from the various viewers who chose to opt-in can be substantially different in terms of video quality, frame rate, etc. As a result, the facial video data can be scaled, rotated, and otherwise adjusted to improve consistency. Human factors further play into the capture of the facial video data. The facial data that is captured might or might not be relevant to the video media presentation being displayed. For example, the viewer might not be paying attention, might be fidgeting, might be distracted by an object or event near the viewer, or otherwise inattentive to the video media presentation. The behavior exhibited by the viewer can prove challenging to analyze due to viewer actions including eating, speaking to another person or persons, speaking on the phone, etc. The videos collected from the viewers might also include other artifacts that pose challenges during the analysis of the video data. The artifacts can include such items as eyeglasses (because of reflections), eye patches, jewelry, and clothing that occludes or obscures the viewer's face. Similarly, a viewer's hair or hair covering can present artifacts by obscuring the viewer's eyes and/or face.

The captured facial data can be analyzed using the facial action coding system (FACS). The FACS seeks to define groups or taxonomies of facial movements of the human face. The FACS encodes movements of individual muscles of the face, where the muscle movements often include slight, instantaneous changes in facial appearance. The FACS encoding is commonly performed by trained observers, but can also be performed on automated, computer-based systems. Analysis of the FACS encoding can be used to determine emotions of the persons whose facial data is captured in the videos. The FACS is used to encode a wide range of facial expressions that are anatomically possible for the human face. The FACS encodings include action units (AUs) and related temporal segments that are based on the captured facial expression. The AUs are open to higher order interpretation and decision-making. For example, the AUs can be used to recognize emotions experienced by the observed person. Emotion-related facial actions can be identified using the emotional facial action coding system (EM-FACS) and the facial action coding system affect interpretation dictionary (FACSAID), for example. For a given emotion, specific action units can be related to the emotion. For example, the emotion of anger can be related to AUs 4, 5, 7, and 23, while happiness can be related to AUs 6 and 12. Other mappings of emotions to AUs have also been previously associated. The coding of the AUs can include an intensity scoring that ranges from A (trace) to E (maximum). The AUs can be used for analyzing images to identify patterns indicative of a particular mental and/or emotional state. The AUs range in number from 0 (neutral face) to 98 (fast up-down look). The AUs include so-called main codes (inner brow raiser, lid tightener, etc.), head movement codes (head turn left, head up, etc.), eye movement codes (eyes turned left, eyes up, etc.), visibility codes (eyes not visible, entire face not visible, etc.), and gross behavior codes (sniff, swallow, etc.). Emotion scoring can be included where intensity is evaluated as well as specific emotions, moods, or mental states.

The coding of faces identified in videos captured of people observing an event can be automated. The automated systems can detect facial AUs or discrete emotional states. The emotional states can include amusement, fear, anger, disgust, surprise, and sadness, for example. The automated systems can be based on a probability estimate from one or more classifiers, where the probabilities can correlate with an intensity of an AU or an expression. The classifiers can be used to identify into which of a set of categories a given observation can be placed. For example, the classifiers can be used to determine a probability that a given AU or expression is present in a given frame of a video. The classifiers can be used as part of a supervised machine learning technique where the machine learning technique can be trained using "known good" data. Once trained, the machine learning technique can proceed to classify new data that is captured.

The supervised machine learning models can be based on support vector machines (SVMs). An SVM can have an associated learning model that is used for data analysis and pattern analysis. For example, an SVM can be used to classify data that can be obtained from collected videos of people experiencing a media presentation. An SVM can be trained using "known good" data that is labeled as belonging to one of two categories (e.g. smile and no-smile). The SVM can build a model that assigns new data into one of the two categories. The SVM can construct one or more hyperplanes that can be used for classification. The hyperplane that has the largest distance from the nearest training point can be determined to have the best separation. The largest separation can improve the classification technique by increasing the probability that a given data point can be properly classified.

In another example, a histogram of oriented gradients (HoG) can be computed. The HoG can include feature descriptors and can be computed for one or more facial regions of interest. The regions of interest of the face can be located using facial landmark points, where the facial landmark points can include outer edges of nostrils, outer edges of the mouth, outer edges of eyes, etc. A HoG for a given region of interest can count occurrences of gradient orientation within a given section of a frame from a video, for example. The gradients can be intensity gradients and can be used to describe an appearance and a shape of a local object. The HoG descriptors can be determined by dividing an image into small, connected regions, also called cells. A histogram of gradient directions or edge orientations can be computed for pixels in the cell. Histograms can be contrast-normalized based on intensity across a portion of the image or the entire image, thus reducing any influence from illumination or shadowing changes between and among video frames. The HoG can be computed on the image or on an adjusted version of the image, where the adjustment of the image can include scaling, rotation, etc. For example, the image can be adjusted by flipping the image around a vertical line through the middle of a face in the image. The symmetry plane of the image can be determined from the tracker points and landmarks of the image.

Embodiments include identifying a first face and a second face within the facial data. Identifying and analyzing can be accomplished without further interaction with the cloud environment, in coordination with the cloud environment, and so on. In an embodiment, an automated facial analysis system identifies five facial actions or action combinations in order to detect spontaneous facial expressions for media research purposes. Based on the facial expressions that are detected, a determination can be made with regard to the effectiveness of a given video media presentation, for example. The system can detect the presence of the AUs or the combination of AUs in videos collected from a plurality of people. The facial analysis technique can be trained using a web-based framework to crowdsource videos of people as they watch online video content. The video can be streamed at a fixed frame rate to a server. Human labelers can code for the presence or absence of facial actions including symmetric smile, unilateral smile, asymmetric smile, and so on. The trained system can then be used to automatically code the facial data collected from a plurality of viewers experiencing video presentations (e.g. television programs).

Spontaneous asymmetric smiles can be detected in order to understand viewer experiences. Related literature indicates that as many asymmetric smiles occur on the right hemi face as do on the left hemi face, for spontaneous expressions. Detection can be treated as a binary classification problem, where images that contain a right asymmetric expression are used as positive (target class) samples and all other images as negative (non-target class) samples. Classifiers perform the classification, including classifiers such as support vector machines (SVM) and random forests. Random forests can include ensemble-learning methods that use multiple learning algorithms to obtain better predictive performance. Frame-by-frame detection can be performed to recognize the presence of an asymmetric expression in each frame of a video. Facial points can be detected, including the top of the mouth and the two outer eye corners. The face can be extracted, cropped, and warped into a pixel image of specific dimension (e.g. 96×96 pixels). In embodiments, the inter-ocular distance and vertical scale in the pixel image are fixed. Feature extraction can be performed using computer vision software such as OpenCV™. Feature extraction can be based on the use of HoGs. HoGs can include feature descriptors and can be used to count occurrences of gradient orientation in localized portions or regions of the image. Other techniques can be used for counting occurrences of gradient orientation, including edge orientation histograms, scale-invariant feature transformation descriptors, etc. The AU recognition tasks can also be performed using Local Binary Patterns (LBP) and Local Gabor Binary Patterns (LGBP). The HoG descriptor represents the face as a distribution of intensity gradients and edge directions, and is robust in its ability to translate and scale. Differing patterns, including groupings of cells of various sizes and arranged in variously sized cell blocks, can be used. For example, 4×4 cell blocks of 8×8 pixel cells with an overlap of half of the block can be used. Histograms of channels can be used, including nine channels or bins evenly spread over 0-180 degrees. In this example, the HoG descriptor on a 96×96 image is 25 blocks×16 cells×9 bins=3600, the latter quantity representing the dimension. AU occurrences can be rendered. The videos can be grouped into demographic datasets based on nationality and/or other demographic parameters for further detailed analysis.

Figure 6:
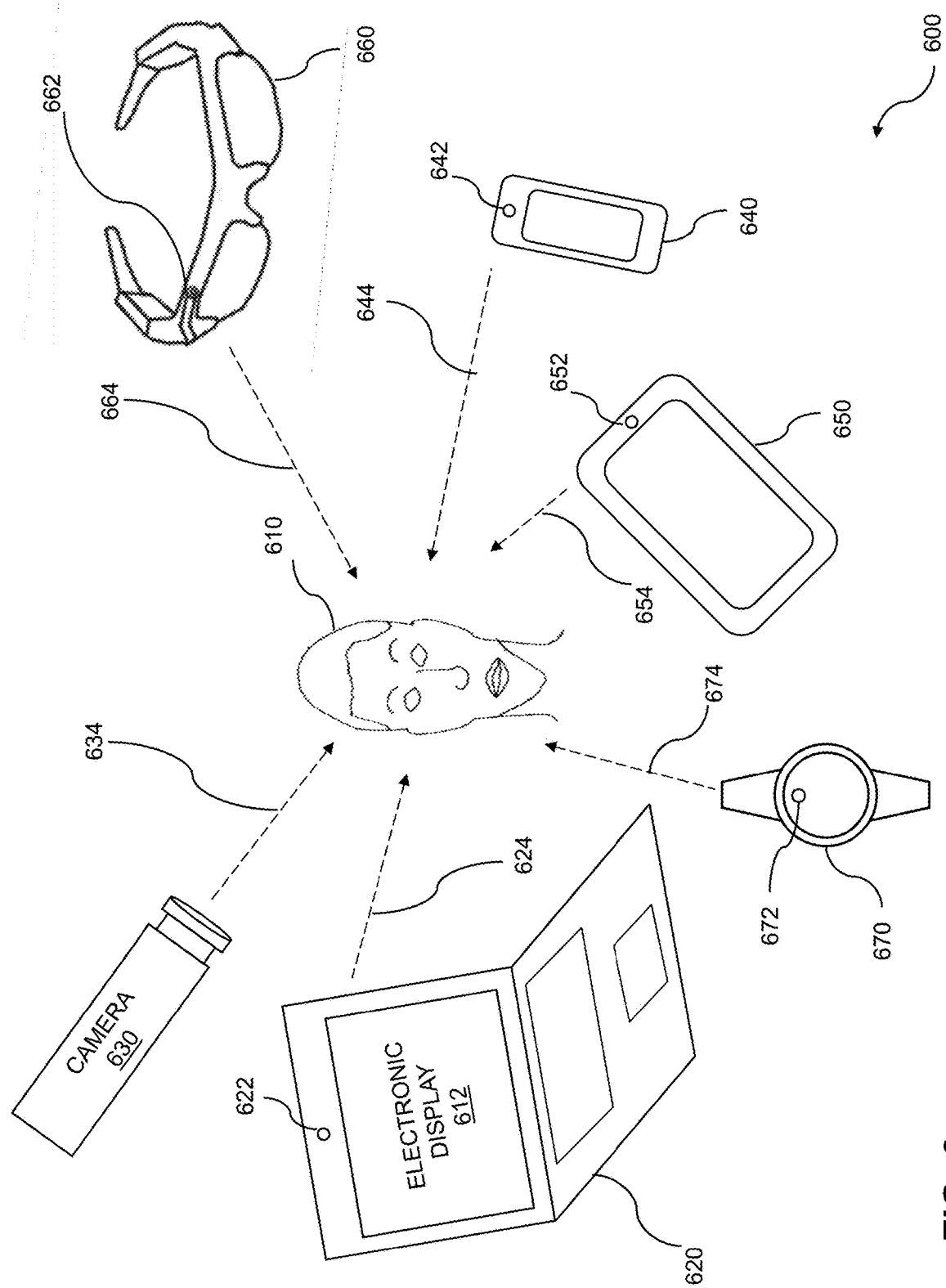
FIG. 6 shows example image collection including multiple mobile devices.

FIG. 6 shows example image collection including multiple mobile devices 600. The images that can be collected can be analyzed to perform mental state analysis and determine weights and image classifiers. The weights and the image classifiers can be used to infer an emotional metric. The multiple mobile devices can be used to collect video data on a person. While one person is shown, in practice, the video data on any number of people can be collected. A user 610 can be observed as she or he is performing a task, experiencing an event, viewing a media presentation, and so on. The user 610 can be viewing a media presentation or another form of displayed media. The one or more video presentations can be visible to a plurality of people instead of an individual user. If the plurality of people is viewing a media presentation, then the media presentations can be displayed on an electronic display 612. The data collected on the user 610 or on a plurality of users can be in the form of one or more videos. The plurality of videos can be of people who are experiencing different situations. Some example situations can include the user or plurality of users viewing one or more robots performing various tasks. The situations could also include exposure to media such as advertisements, political messages, news programs, and so on. As noted before, video data can be collected on one or more users in substantially identical or different situations. The data collected on the user 610 can be analyzed and viewed for a variety of purposes, including expression analysis. The electronic display 612 can be on a laptop computer 620 as shown, a tablet computer 650, a cell phone 640, a television, a mobile monitor, or any other type of electronic device. In a certain embodiment, expression data is collected on a mobile device such as a cell phone 640, a tablet computer 650, a laptop computer 620, or a watch 670. Thus, the multiple sources can include at least one mobile device such as a cell phone 640 or a tablet computer 650, or a wearable device such as a watch 670 or glasses 660. A mobile device can include a front-side camera and/or a back-side camera that can be used to collect expression data. Sources of expression data can include a webcam 622, a phone camera 642, a tablet camera 652, a wearable camera 662, and a mobile camera 630. A wearable camera can comprise various camera devices such as the watch camera 672.

As the user 610 is monitored, the user 610 might move due to the nature of the task, boredom, discomfort, distractions, or for another reason. As the user moves, the camera with a view of the user's face can change. Thus, as an example, if the user 610 is looking in a first direction, the line of sight 624 from the webcam 622 is able to observe the individual's face, but if the user is looking in a second direction, the line of sight 634 from the mobile camera 630 is able to observe the individual's face. Further, in other embodiments, if the user is looking in a third direction, the line of sight 644 from the phone camera 642 is able to observe the individual's face, and if the user is looking in a fourth direction, the line of sight 654 from the tablet camera 652 is able to observe the individual's face. If the user is looking in a fifth direction, the line of sight 664 from the wearable camera 662, which can be a device such as the glasses 660 shown and can be worn by another user or an observer, is able to observe the individual's face. If the user is looking in a sixth direction, the line of sight 674 from the wearable watch-type device 670 with a camera 672 included on the device, is able to observe the individual's face. In other embodiments, the wearable device is another device, such as an earpiece with a camera, a helmet or hat with a camera, a clip-on camera attached to clothing, or any other type of wearable device with a camera or another sensor for collecting expression data. The user 610 can also employ a wearable device including a camera for gathering contextual information and/or collecting expression data on other users. Because the user 610 can move her or his head, the facial data can be collected intermittently when the individual is looking in a direction of a camera. In some cases, multiple people are included in the view from one or more cameras, and some embodiments include filtering out faces of one or more other people to determine whether the user 610 is looking toward a camera. All or some of the expression data can be continuously or sporadically available from these various devices and other devices.

The captured video data can include facial expressions and can be analyzed on a computing device, such as the video capture device or on another separate device. The analysis of the video data can include the use of a classifier. For example, the video data can be captured using one of the mobile devices discussed above and sent to a server or another computing device for analysis. However, the captured video data including expressions can also be analyzed on the device which performed the capturing. For example, the analysis can be performed on a mobile device, where the videos were obtained with the mobile device and wherein the mobile device includes one or more of a laptop computer, a tablet, a PDA, a smartphone, a wearable device, and so on. In another embodiment, the analyzing comprises using a classifier on a server or another computing device other than the capturing device. The result of the analyzing can be used to infer one or more emotional metrics.

Figure 7:
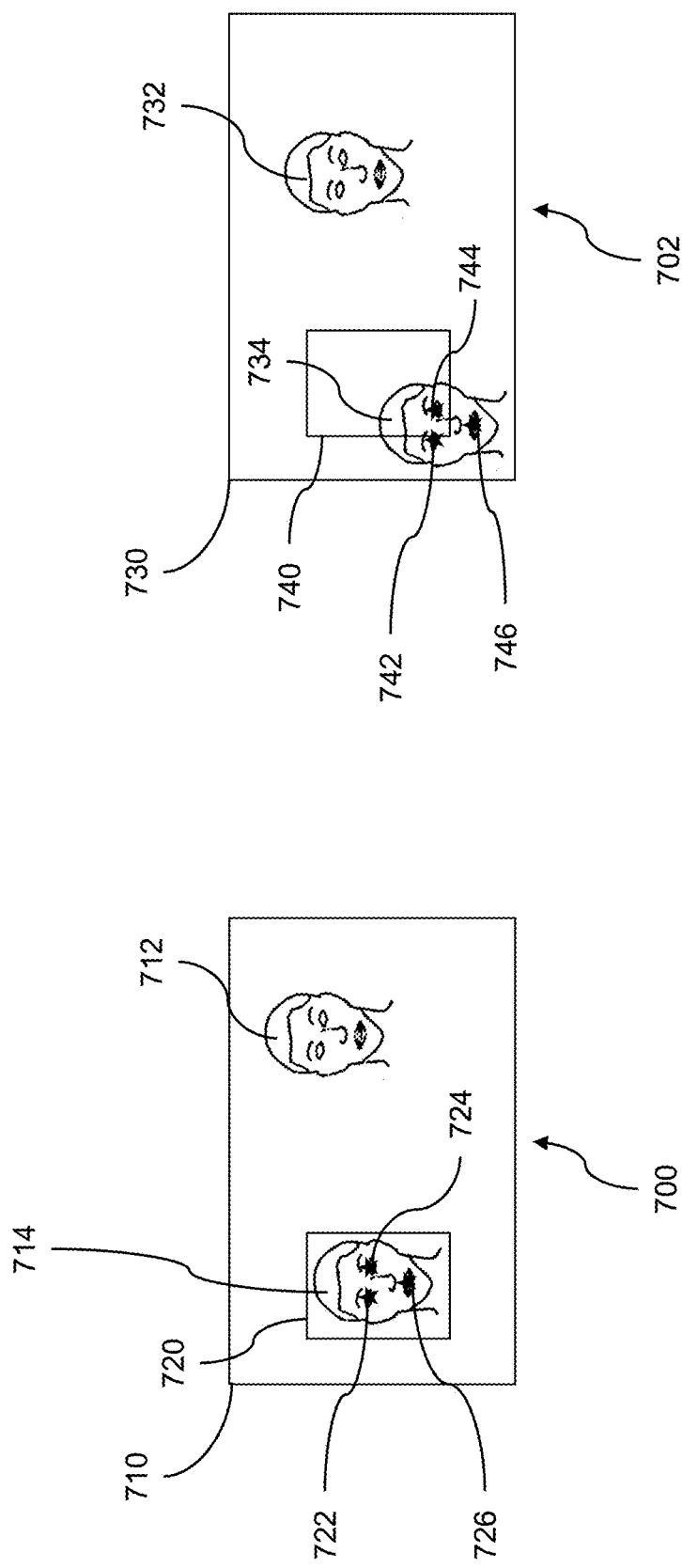
FIG. 7 illustrates feature extraction for multiple faces.

FIG. 7 illustrates feature extraction for multiple faces. The features can be evaluated within a deep learning environment. The feature extraction for multiple faces can be performed for faces that can be detected in multiple images. The images can be analyzed for mental states and/or facial expressions. A plurality of images can be received of an individual viewing an electronic display. A face can be identified in an image, based on the use of classifiers. The plurality of images can be evaluated to determine mental states and/or facial expressions of the individual. The feature extraction can be performed by analysis using one or more processors, using one or more video collection devices, and by using a server. The analysis device can be used to perform face detection for a second face, as well as for facial tracking of the first face. One or more videos can be captured, where the videos contain one or more faces. The video or videos that contain the one or more faces can be partitioned into a plurality of frames, and the frames can be analyzed for the detection of the one or more faces. The analysis of the one or more video frames can be based on one or more classifiers. A classifier can be an algorithm, heuristic, function, or piece of code that can be used to identify into which of a set of categories a new or particular observation, sample, datum, etc. should be placed. The decision to place an observation into a category can be based on training the algorithm or piece of code, by analyzing a known set of data, known as a training set. The training set can include data for which category memberships of the data can be known. The training set can be used as part of a supervised training technique. If a training set is not available, then a clustering technique can be used to group observations into categories. The latter approach, or unsupervised learning, can be based on a measure (i.e. distance) of one or more inherent similarities among the data that is being categorized. When the new observation is received, then the classifier can be used to categorize the new observation. Classifiers can be used for many analysis applications including analysis of one or more faces. The use of classifiers can be the basis of analyzing the one or more faces for gender, ethnicity, and age; for detection of one or more faces in one or more videos; for detection of facial features, for detection of facial landmarks, and so on. The observations can be analyzed based on one or more of a set of quantifiable properties. The properties can be described as features and explanatory variables and can include various data types that can include numerical (integer-valued, real-valued), ordinal, categorical, and so on. Some classifiers can be based on a comparison between an observation and prior observations, as well as based on functions such as a similarity function, a distance function, and so on.

Classification can be based on various types of algorithms, heuristics, codes, procedures, statistics, and so on. Many techniques exist for performing classification. This classification of one or more observations into one or more groups can be based on distributions of the data values, probabilities, and so on. Classifiers can be binary, multiclass, linear, and so on. Algorithms for classification can be implemented using a variety of techniques, including neural networks, kernel estimation, support vector machines, use of quadratic surfaces, and so on. Classification can be used in many application areas such as computer vision, speech and handwriting recognition, and so on. Classification can be used for biometric identification of one or more people in one or more frames of one or more videos.

Returning to FIG. 7, the detection of the first face, the second face, and multiple faces can include identifying facial landmarks, generating a bounding box, and prediction of a bounding box and landmarks for a next frame, where the next frame can be one of a plurality of frames of a video containing faces. A first video frame 700 includes a frame boundary 710, a first face 712, and a second face 714. The video frame 700 also includes a bounding box 720. Facial landmarks can be generated for the first face 712. Face detection can be performed to initialize a second set of locations for a second set of facial landmarks for a second face within the video. Facial landmarks in the video frame 700 can include the facial landmarks 722, 724, and 726. The facial landmarks can include corners of a mouth, corners of eyes, eyebrow corners, the tip of the nose, nostrils, chin, the tips of ears, and so on. The performing of face detection on the second face can include performing facial landmark detection with the first frame from the video for the second face and can include estimating a second rough bounding box for the second face based on the facial landmark detection. The estimating of a second rough bounding box can include the bounding box 720. Bounding boxes can also be estimated for one or more other faces within the boundary 710. The bounding box can be refined, as can one or more facial landmarks. The refining of the second set of locations for the second set of facial landmarks can be based on localized information around the second set of facial landmarks. The bounding box 720 and the facial landmarks 722, 724, and 726 can be used to estimate future locations for the second set of locations for the second set of facial landmarks in a future video frame from the first video frame.

A second video frame 702 is also shown. The second video frame 702 includes a frame boundary 730, a first face 732, and a second face 734. The second video frame 702 also includes a bounding box 740 and the facial landmarks 742, 744, and 746. In other embodiments, multiple facial landmarks are generated and used for facial tracking of the two or more faces of a video frame, such as the shown second video frame 702. Facial points from the first face can be distinguished from other facial points. In embodiments, the other facial points include facial points of one or more other faces. The facial points can correspond to the facial points of the second face. The distinguishing of the facial points of the first face and the facial points of the second face can be used to distinguish between the first face and the second face, to track either or both of the first face and the second face, and so on. Other facial points can correspond to the second face. As mentioned above, multiple facial points can be determined within a frame. One or more of the other facial points that are determined can correspond to a third face. The location of the bounding box 740 can be estimated, where the estimating can be based on the location of the generated bounding box 720 shown in the first video frame 700. The three facial landmarks shown, facial landmarks 742, 744, and 746, might lie within the bounding box 740 or might not lie partially or completely within the bounding box 740. For instance, the second face 734 might have moved between the first video frame 700 and the second video frame 702. Based on the accuracy of the estimating of the bounding box 740, a new estimation can be determined for a third, future frame from the video, and so on. The evaluation can be performed, all or in part, on semiconductor based logic.

Figure 8:
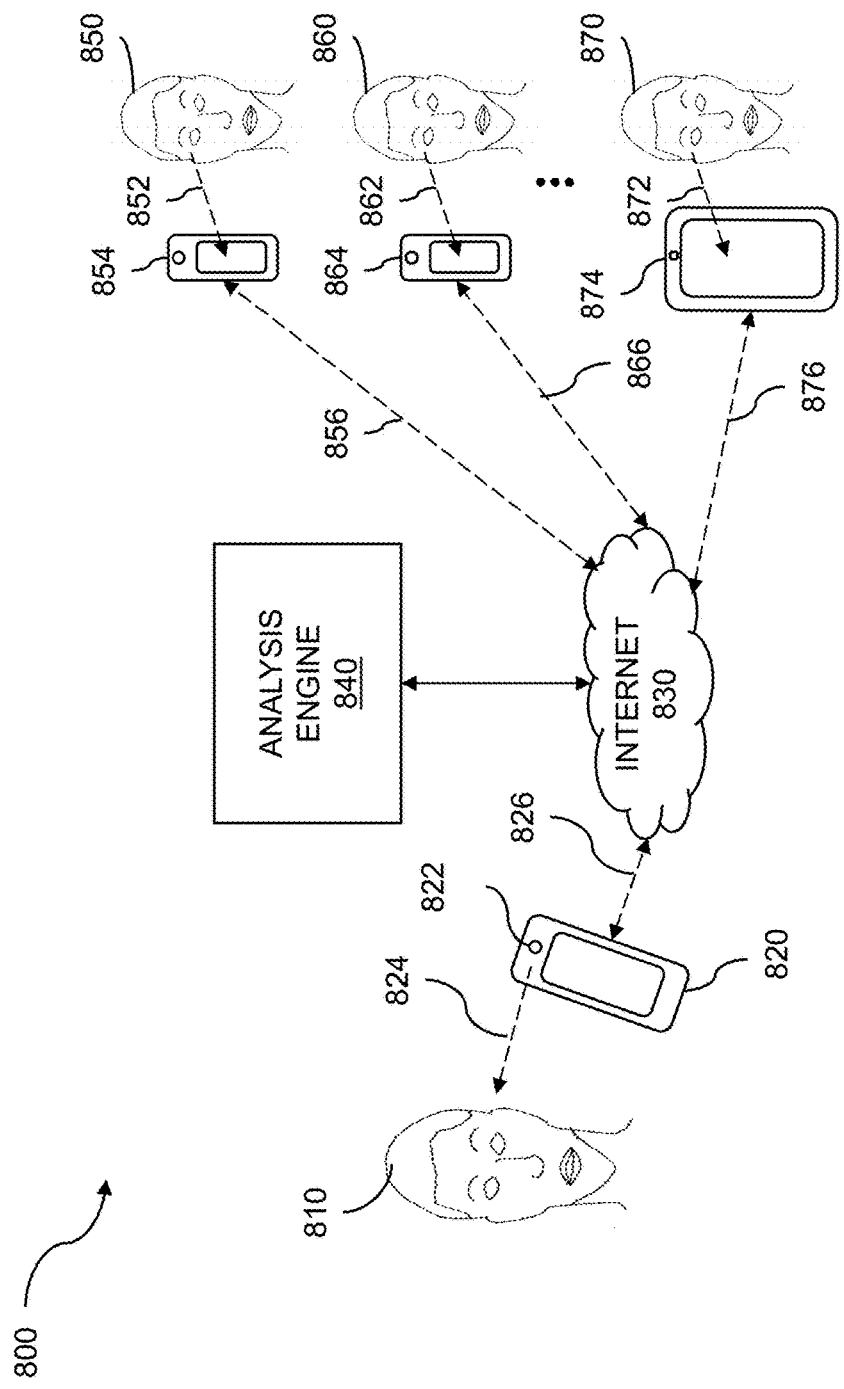
FIG. 8 shows live streaming of social video.

FIG. 8 shows live streaming of social video. The living streaming can be used within a deep learning environment. Analysis of live streaming of social video can be performed using data collected from evaluating images to determine a facial expression and/or mental state. A plurality of images of an individual viewing an electronic display can be received. A face can be identified in an image, based on the use of classifiers. The plurality of images can be evaluated to determine facial expressions and/or mental states of the individual. The streaming and analysis can be facilitated by a video capture device, a local server, a remote server, a semiconductor based logic, and so on. The streaming can be live streaming and can include mental state analysis, mental state event signature analysis, etc. Live streaming video is an example of one-to-many social media, where video can be sent over the Internet from one person to a plurality of people using a social media app and/or platform. Live streaming is one of numerous popular techniques used by people who want to disseminate ideas, send information, provide entertainment, share experiences, and so on. Some of the live streams can be scheduled, such as webcasts, online classes, sporting events, news, computer gaming, or video conferences, while others can be impromptu streams that are broadcasted as needed or when desirable. Examples of impromptu live stream videos can range from individuals simply wanting to share experiences with their social media followers, to live coverage of breaking news, emergencies, or natural disasters. The latter coverage is known as mobile journalism and is becoming increasingly common. With this type of coverage, "reporters" can use networked, portable electronic devices to provide mobile journalism content to a plurality of social media followers. Such reporters can be quickly and inexpensively deployed as the need or desire arises.

Several live streaming social media apps and platforms can be used for transmitting video. One such video social media app is Meerkat™ that can link with a user's Twitter™ account. Meerkat™ enables a user to stream video using a handheld, networked electronic device coupled to video capabilities. Viewers of the live stream can comment on the stream using tweets that can be seen by and responded to by the broadcaster. Another popular app is Periscope™ that can transmit a live recording from one user to that user's Periscope™ account and other followers. The Periscope™ app can be executed on a mobile device. The user's Periscope™ followers can receive an alert whenever that user begins a video transmission. Another live-stream video platform is Twitch™ that can be used for video streaming of video gaming and broadcasts of various competitions and events.

The example 800 shows a user 810 broadcasting a video live-stream to one or more people as shown by the person 850, the person 860, and the person 870. A portable, network-enabled electronic device 820 can be coupled to a front-side camera 822. The portable electronic device 820 can be a smartphone, a PDA, a tablet, a laptop computer, and so on. The camera 822 coupled to the device 820 can have a line-of-sight view 824 to the user 810 and can capture video of the user 810. The captured video can be sent to a recommendation or analysis engine 840 using a network link 826 to the Internet 830. The network link can be a wireless link, a wired link, and so on. The analysis engine 840 can recommend an app and/or platform to the user 810 that can be supported by the server and can be used to provide a video live-stream to one or more followers of the user 810. In the example 800, the user 810 has three followers: the person 850, the person 860, and the person 870. Each follower has a line-of-sight view to a video screen on a portable, networked electronic device. In other embodiments, one or more followers follow the user 810 using any other networked electronic device, including a computer. In the example 800, the person 850 has a line-of-sight view 852 to the video screen of a device 854; the person 860 has a line-of-sight view 862 to the video screen of a device 864, and the person 870 has a line-of-sight view 872 to the video screen of a device 874. The portable electronic devices 854, 864, and 874 can each be a smartphone, a PDA, a tablet, and so on. Each portable device can receive the video stream being broadcasted by the user 810 through the Internet 830 using the app and/or platform that can be recommended by the analysis engine 840. The device 854 can receive a video stream using the network link 856, the device 864 can receive a video stream using the network link 866, the device 874 can receive a video stream using the network link 876, and so on. The network link can be a wireless link, a wired link, a hybrid link, and so on. Depending on the app and/or platform that can be recommended by the analysis engine 840, one or more followers, such as the followers 850, 860, 870, and so on, can reply to, comment on, and otherwise provide feedback to the user 810 using their devices 854, 864, and 874, respectively. In embodiments, mental state and/or facial expression analysis is performed on each follower (850, 860, and 870). An aggregate viewership score of the content generated by the user 810 can be calculated. The viewership score can be used to provide a ranking of the user 810 on a social media platform. In such an embodiment, users that provide more engaging and more frequently viewed content receive higher ratings.

Figure 9:
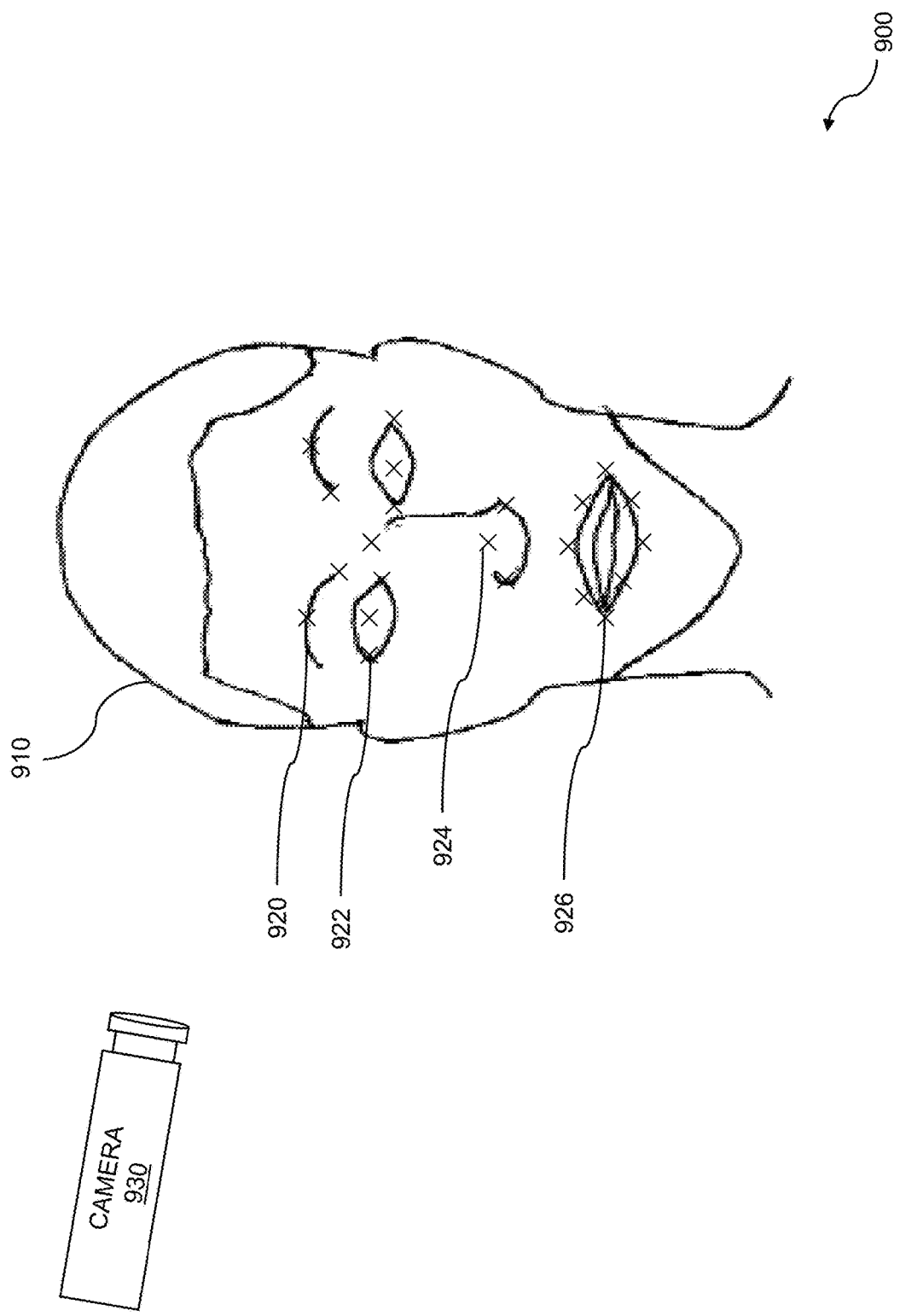
FIG. 9 shows example facial data collection including landmarks.

FIG. 9 shows example facial data collection including landmarks. The landmarks can be evaluated by a multi-layer analysis system. The collecting of facial data including landmarks can be performed for images that have been collected of an individual. The collected images can be analyzed for mental states and/or facial expressions. A plurality of images of an individual viewing an electronic display can be received. A face can be identified in an image, based on the use of classifiers. The plurality of images can be evaluated to determine mental states and/or facial expressions of the individual. In the example 900, facial data including facial landmarks can be collected using a variety of electronic hardware and software techniques. The collecting of facial data including landmarks can be based on sub-sectional components of a population. The sub-sectional components can be used with performing the evaluation of content of the face, identifying facial landmarks, etc. The sub-sectional components can be used to provide a context. A face 910 can be observed using a camera 930 in order to collect facial data that includes facial landmarks. The facial data can be collected from a plurality of people using one or more of a variety of cameras. As previously discussed, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The quality and usefulness of the facial data that is captured can depend on the position of the camera 930 relative to the face 910, the number of cameras used, the illumination of the face, etc. In some cases, if the face 910 is poorly lit or over-exposed (e.g. in an area of bright light), the processing of the facial data to identify facial landmarks might be rendered more difficult. In another example, the camera 930 being positioned to the side of the person might prevent capture of the full face. Artifacts can degrade the capture of facial data. For example, the person's hair, prosthetic devices (e.g. glasses, an eye patch, and eye coverings), jewelry, and clothing can partially or completely occlude or obscure the person's face. Data relating to various facial landmarks can include a variety of facial features. The facial features can comprise an eyebrow 920, an outer eye edge 922, a nose 924, a corner of a mouth 926, and so on. Multiple facial landmarks can be identified from the facial data that is captured. The facial landmarks that are identified can be analyzed to identify facial action units. The action units that can be identified can include AU02 outer brow raiser, AU14 dimpler, AU17 chin raiser, and so on. Multiple action units can be identified. The action units can be used alone and/or in combination to infer one or more mental states and emotions. A similar process can be applied to gesture analysis (e.g. hand gestures) with all of the analysis being accomplished or augmented by a mobile device, a server, semiconductor-based logic, and so on.

Figure 10:
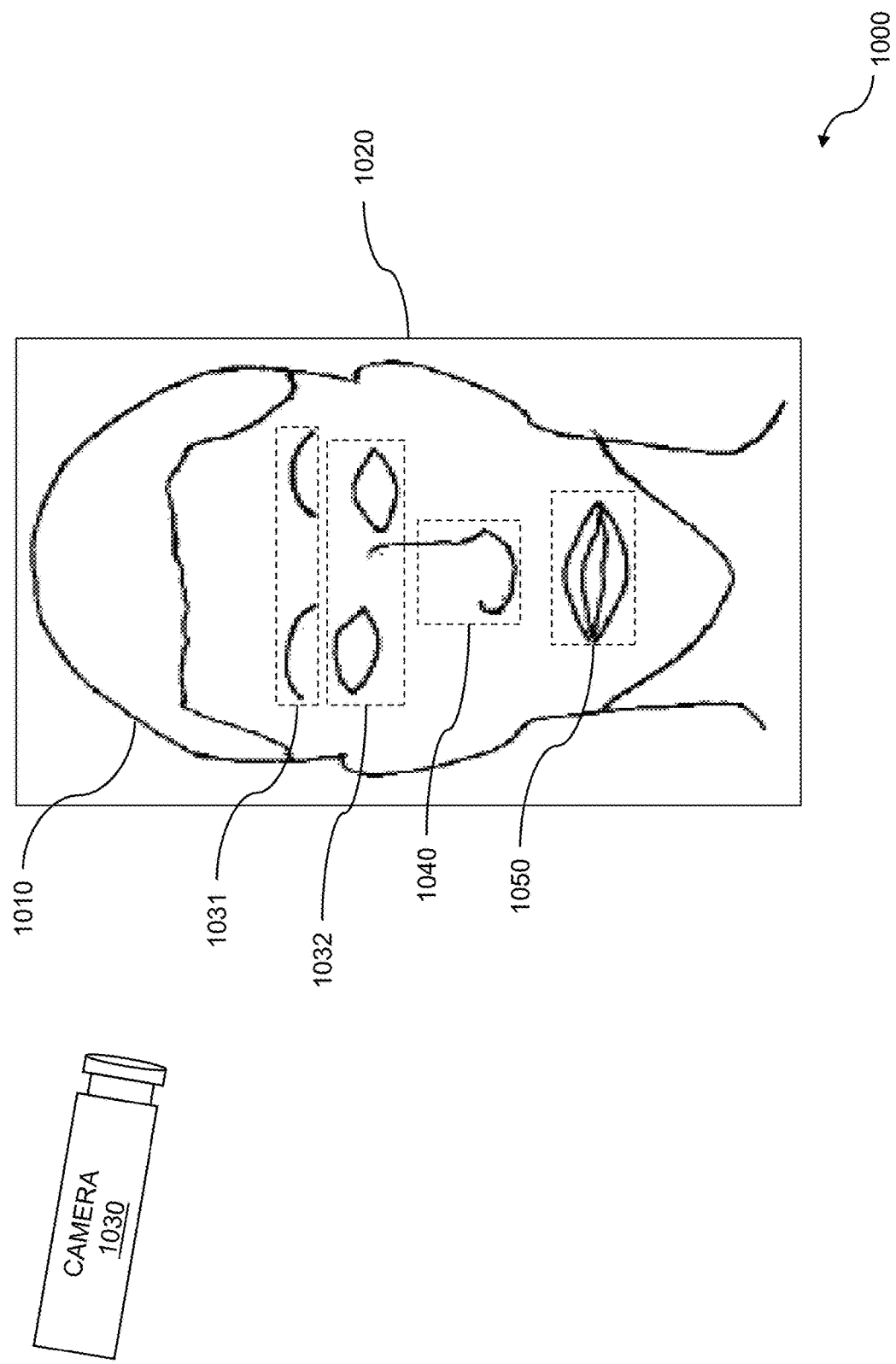
FIG. 10 shows example facial data collection including regions.

FIG. 10 shows example facial data collection including regions. The regions can be evaluated within a deep learning environment. The collecting of facial data including regions can be performed for images collected of an individual. The collected images can be analyzed for mental states and/or facial expressions. A plurality of images of an individual viewing an electronic display can be received. A face can be identified in an image, based on the use of classifiers. The plurality of images can be evaluated to determine mental states and/or facial expressions of the individual. Various regions of a face can be identified and used for a variety of purposes including facial recognition, facial analysis, and so on. The collecting of facial data including regions can be based on sub-sectional components of a population. The sub-sectional components can be used with performing the evaluation of content of the face, identifying facial regions, etc. The sub-sectional components can be used to provide a context. Facial analysis can be used to determine, predict, and estimate mental states and emotions of a person from whom facial data can be collected.

In embodiments, the one or more emotions that can be determined by the analysis can be represented by an image, a figure, an icon, etc. The representative icon can include an emoji or emoticon. One or more emoji can be used to represent a mental state, emotion, or mood of an individual; to represent food, a geographic location, weather, and so on. The emoji can include a static image. The static image can be a predefined size, such as a certain number of pixels. The emoji can include an animated image. The emoji can be based on a GIF or another animation standard. The emoji can include a cartoon representation. The cartoon representation can be any cartoon type, format, etc. that can be appropriate to representing an emoji. In the example 1000, facial data can be collected, where the facial data can include regions of a face. The facial data that is collected can be based on sub-sectional components of a population. When more than one face can be detected in an image, facial data can be collected for one face, some faces, all faces, and so on. The facial data which can include facial regions can be collected using any of a variety of electronic hardware and software techniques. The facial data can be collected using sensors including motion sensors, infrared sensors, physiological sensors, imaging sensors, and so on. A face 1010 can be observed using a camera 1030, a sensor, a combination of cameras and/or sensors, and so on. The camera 1030 can be used to collect facial data that can be used to determine that a face is present in an image. When a face is present in an image, a bounding box 1020 can be placed around the face. Placement of the bounding box around the face can be based on detection of facial landmarks. The camera 1030 can be used to collect facial data from the bounding box 1020, where the facial data can include facial regions. The facial data can be collected from a plurality of people using any of a variety of cameras. As discussed previously, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. As discussed previously, the quality and usefulness of the facial data that is captured can depend on, among other examples, the position of the camera 1030 relative to the face 1010, the number of cameras and/or sensors used, the illumination of the face, any obstructions to viewing the face, and so on.

The facial regions that can be collected by the camera 1030, a sensor, or a combination of cameras and/or sensors can include any of a variety of facial features. Embodiments include determining regions within the face of the individual and evaluating the regions for emotional content. The facial features that can be included in the facial regions that are collected can include eyebrows 1031, eyes 1032, a nose 1040, a mouth 1050, ears, hair, texture, tone, and so on. Multiple facial features can be included in one or more facial regions. The number of facial features that can be included in the facial regions can depend on the desired amount of data to be captured, whether a face is in profile, whether the face is partially occluded or obstructed, etc. The facial regions that can include one or more facial features can be analyzed to determine facial expressions. The analysis of the facial regions can also include determining probabilities of occurrence of one or more facial expressions. The facial features that can be analyzed can also include features such as textures, gradients, colors, and shapes. The facial features can be used to determine demographic data, where the demographic data can include age, ethnicity, culture, and gender. Multiple textures, gradients, colors, shapes, and so on, can be detected by the camera 1030, a sensor, or a combination of cameras and sensors. Texture, brightness, and color, for example, can be used to detect boundaries in an image for detection of a face, facial features, facial landmarks, and so on.

A texture in a facial region can include facial characteristics, skin types, and so on. In some instances, a texture in a facial region can include smile lines, crow's feet, and wrinkles, among others. Another texture that can be used to evaluate a facial region can include a smooth portion of skin such as a smooth portion of a check. A gradient in a facial region can include values assigned to local skin texture, shading, etc. A gradient can be used to encode a texture by computing magnitudes in a local neighborhood or portion of an image. The computed values can be compared to discrimination levels, threshold values, and so on. The gradient can be used to determine gender, facial expression, etc. A color in a facial region can include eye color, skin color, hair color, and so on. A color can be used to determine demographic data, where the demographic data can include ethnicity, culture, age, and gender. A shape in a facial region can include the shape of a face, eyes, nose, mouth, ears, and so on. As with color in a facial region, shape in a facial region can be used to determine demographic data including ethnicity, culture, age, gender, and so on.

The facial regions can be detected based on detection of edges, boundaries, and so on, of features that can be included in an image. The detection can be based on various types of analysis of the image. The features that can be included in the image can include one or more faces. A boundary can refer to a contour in an image plane, where the contour can represent ownership of a particular picture element (pixel) from one object, feature, etc. in the image, to another object, feature, and so on, in the image. An edge can be a distinct, low-level change of one or more features in an image. That is, an edge can be detected based on a change, including an abrupt change such as in color or brightness within an image. In embodiments, image classifiers are used for the analysis. The image classifiers can include algorithms, heuristics, and so on, and can be implemented using functions, classes, subroutines, code segments, etc. The classifiers can be used to detect facial regions, facial features, and so on. As discussed above, the classifiers can be used to detect textures, gradients, color, shapes, and edges, among others. Any classifier can be used for the analysis, including, but not limited to, density estimation, support vector machines (SVM), logistic regression, classification trees, and so on. By way of example, consider facial features that can include the eyebrows 1031. One or more classifiers can be used to analyze the facial regions that can include the eyebrows to determine a probability for either a presence or an absence of an eyebrow furrow. The probability can include a posterior probability, a conditional probability, and so on. The probabilities can be based on Bayesian Statistics or another statistical analysis technique. The presence of an eyebrow furrow can indicate the person from whom the facial data was collected is annoyed, confused, unhappy, and so on. In another example, consider facial features that can include a mouth 1050. One or more classifiers can be used to analyze the facial region that can include the mouth to determine a probability for either a presence or an absence of mouth edges turned up to form a smile. Multiple classifiers can be used to determine one or more facial expressions.

Figure 11:
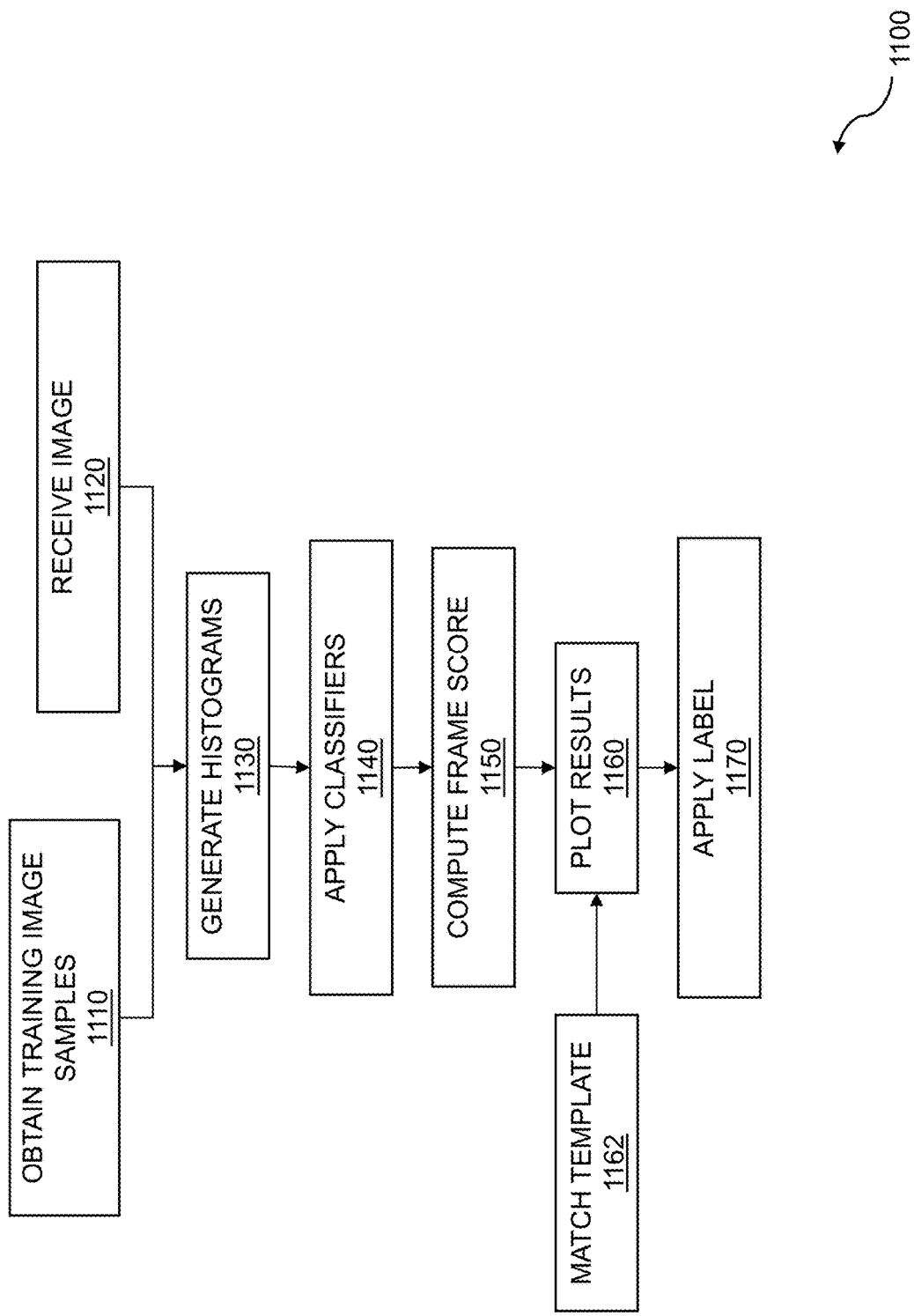
FIG. 11 is a flow diagram for detecting facial expressions.

FIG. 11 is a flow diagram for detecting facial expressions. The detection of facial expressions can be performed for data collected from images of an individual and used within a deep learning environment. The collected images can be analyzed for mental states and/or facial expressions. A plurality of images can be received of an individual viewing an electronic display. A face can be identified in an image, based on the use of classifiers. The plurality of images can be evaluated to determine the mental states and/or facial expressions the individual. The flow 1100, or portions thereof, can be implemented in semiconductor logic, can be accomplished using a mobile device, can be accomplished using a server device, and so on. The flow 1100 can be used to automatically detect a wide range of facial expressions. A facial expression can produce strong emotional signals that can indicate valence and discrete emotional states. The discrete emotional states can include contempt, doubt, defiance, happiness, fear, anxiety, and so on. The detection of facial expressions can be based on the location of facial landmarks. The detection of facial expressions can be based on determination of action units (AU), where the action units are determined using FACS coding. The AUs can be used singly or in combination to identify facial expressions. Based on the facial landmarks, one or more AUs can be identified by number and intensity. For example, AU12 can be used to code a lip corner puller and can be used to infer a smirk.

The flow 1100 begins by obtaining training image samples 1110. The image samples can include a plurality of images of one or more people. Human coders who are trained to correctly identify AU codes based on the FACS can code the images. The training, or "known good," images can be used as a basis for training a machine learning technique. Once trained, the machine learning technique can be used to identify AUs in other images that can be collected using a camera, a sensor, and so on. The flow 1100 continues with receiving an image 1120. The image 1120 can be received from a camera, a sensor, and so on. As previously discussed, the camera or cameras can include a webcam, where a webcam can include a video camera, a still camera, a thermal imager, a CCD device, a phone camera, a three-dimensional camera, a depth camera, a light field camera, multiple webcams used to show different views of a person, or any other type of image capture apparatus that can allow captured data to be used in an electronic system. The image that is received can be manipulated in order to improve the processing of the image. For example, the image can be cropped, scaled, stretched, rotated, flipped, etc. in order to obtain a resulting image that can be analyzed more efficiently. Multiple versions of the same image can be analyzed. In some cases, the manipulated image and a flipped or mirrored version of the manipulated image can be analyzed alone and/or in combination to improve analysis. The flow 1100 continues with generating histograms 1130 for the training images and the one or more versions of the received image. The histograms can be based on a HoG or another histogram. As described in previous paragraphs, the HoG can include feature descriptors and can be computed for one or more regions of interest in the training images and the one or more received images. The regions of interest in the images can be located using facial landmark points, where the facial landmark points can include outer edges of nostrils, outer edges of the mouth, outer edges of eyes, etc. A HoG for a given region of interest can count occurrences of gradient orientation within a given section of a frame from a video.

The flow 1100 continues with applying classifiers 1140 to the histograms. The classifiers can be used to estimate probabilities, where the probabilities can correlate with an intensity of an AU or an expression. In some embodiments, the choice of classifiers used is based on the training of a supervised learning technique to identify facial expressions. The classifiers can be used to identify into which of a set of categories a given observation can be placed. The classifiers can be used to determine a probability that a given AU or expression is present in a given image or frame of a video. In various embodiments, the one or more AUs that are present include AU01 inner brow raiser, AU12 lip corner puller, AU38 nostril dilator, and so on. In practice, the presence or absence of multiple AUs can be determined. The flow 1100 continues with computing a frame score 1150. The score computed for an image, where the image can be a frame from a video, can be used to determine the presence of a facial expression in the image or video frame. The score can be based on one or more versions of the image 1120 or a manipulated image. The score can be based on a comparison of the manipulated image to a flipped or mirrored version of the manipulated image. The score can be used to predict a likelihood that one or more facial expressions are present in the image. The likelihood can be based on computing a difference between the outputs of a classifier used on the manipulated image and on the flipped or mirrored image, for example. The classifier that is used can be used to identify symmetrical facial expressions (e.g. smile), asymmetrical facial expressions (e.g. outer brow raiser), and so on.

The flow 1100 continues with plotting results 1160. The results that are plotted can include one or more scores for one or more frames computed over a given time t. For example, the plotted results can include classifier probability results from analysis of HoGs for a sequence of images and video frames. The plotted results can be matched with a template 1162. The template can be temporal and can be represented by a centered box function or another function. A best fit with one or more templates can be found by computing a minimum error. Other best-fit techniques can include polynomial curve fitting, geometric curve fitting, and so on. The flow 1100 continues with applying a label 1170. The label can be used to indicate that a particular facial expression has been detected in the one or more images or video frames which constitute the image 1120 that was received. The label can be used to indicate that any of a range of facial expressions has been detected, including a smile, an asymmetric smile, a frown, and so on. Various steps in the flow 1100 may be changed in order, repeated, omitted, or the like without departing from the disclosed concepts. Various embodiments of the flow 1100 can be included in a computer program product embodied in a non-transitory computer readable medium that includes code executable by one or more processors. Various embodiments of the flow 1100, or portions thereof, can be included on a semiconductor chip and implemented in special purpose logic, programmable logic, and so on.

Figure 12:
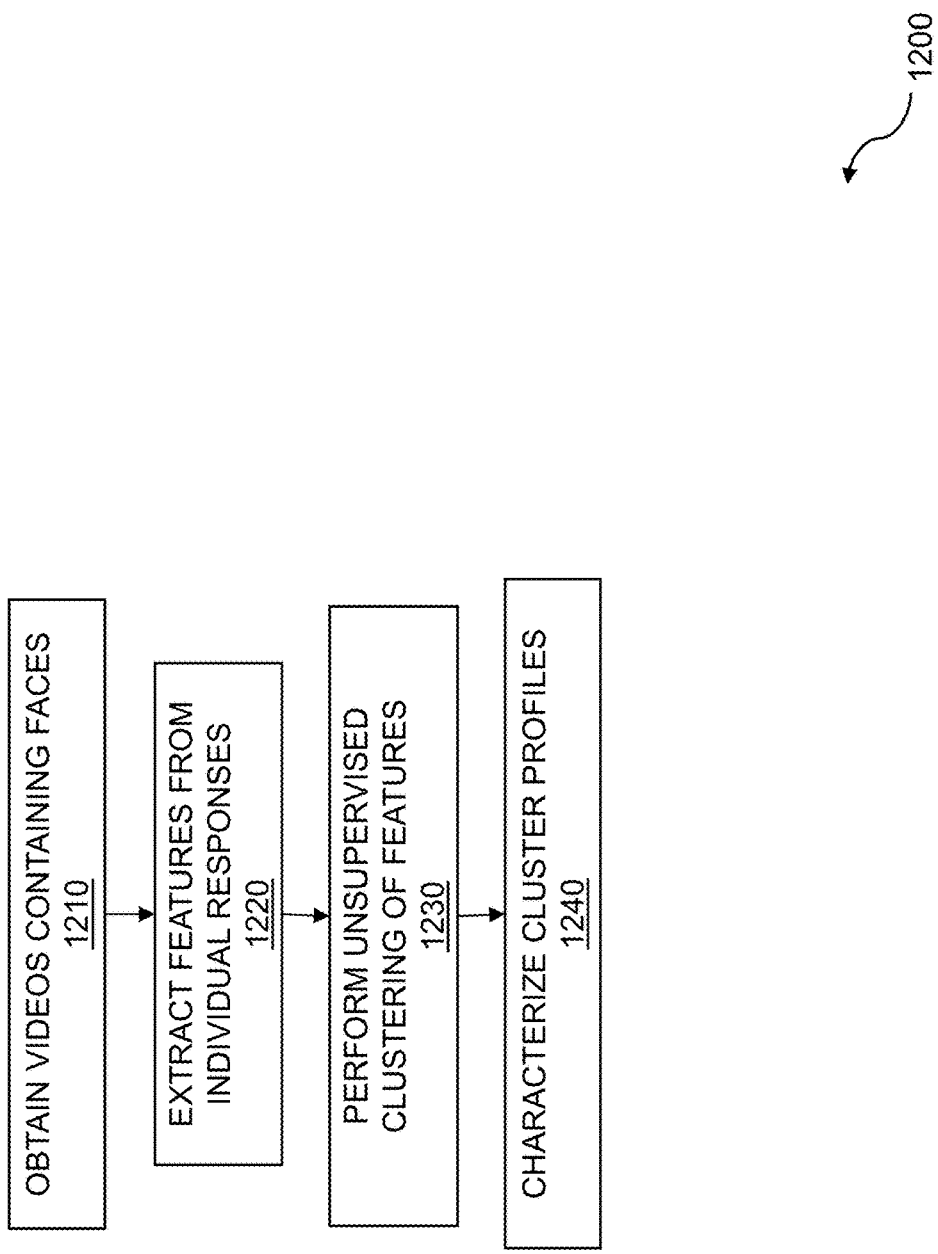
FIG. 12 is a flow diagram for the large-scale clustering of facial events.

FIG. 12 is a flow diagram for the large-scale clustering of facial events. The large-scale clustering of facial events can be performed for data collected from images of an individual. The collected images can be analyzed for mental states and/or facial expressions. A plurality of images can be received of an individual viewing an electronic display. A face can be identified in an image, based on the use of classifiers. The plurality of images can be evaluated to determine the mental states and/or facial expressions of the individual. The clustering and evaluation of facial events can be augmented using a mobile device, a server, semiconductor based logic, and so on. As discussed above, collection of facial video data from one or more people can include a web-based framework. The web-based framework can be used to collect facial video data from large numbers of people located over a wide geographic area. The web-based framework can include an opt-in feature that allows people to agree to facial data collection. The web-based framework can be used to render and display data to one or more people and can collect data from the one or more people. For example, the facial data collection can be based on showing one or more viewers a video media presentation through a website. The web-based framework can be used to display the video media presentation or event and to collect videos from multiple viewers who are online. That is, the collection of videos can be crowdsourced from those viewers who elected to opt-in to the video data collection. The video event can be a commercial, a political ad, an educational segment, and so on.

The flow 1200 begins with obtaining videos containing faces 1210. The videos can be obtained using one or more cameras, where the cameras can include a webcam coupled to one or more devices employed by the one or more people using the web-based framework. The flow 1200 continues with extracting features from the individual responses 1220. The individual responses can include videos containing faces observed by the one or more webcams. The features that are extracted can include facial features such as an eyebrow, a nostril, an eye edge, a mouth edge, and so on. The feature extraction can be based on facial coding classifiers, where the facial coding classifiers output a probability that a specified facial action has been detected in a given video frame. The flow 1200 continues with performing unsupervised clustering of features 1230. The unsupervised clustering can be based on an event. The unsupervised clustering can be based on a K-Means, where the K of the K-Means can be computed using a Bayesian Information Criterion (BICk), for example, to determine the smallest value of K that meets system requirements. Any other criterion for K can be used. The K-Means clustering technique can be used to group one or more events into various respective categories.

The flow 1200 continues with characterizing cluster profiles 1240. The profiles can include a variety of facial expressions such as smiles, asymmetric smiles, eyebrow raisers, eyebrow lowerers, etc. The profiles can be related to a given event. For example, a humorous video can be displayed in the web-based framework and the video data of people who have opted-in can be collected. The characterization of the collected and analyzed video can depend in part on the number of smiles that occurred at various points throughout the humorous video. The number of smiles resulting from people viewing a humorous video can be compared to various demographic groups, where the groups can be formed based on geographic location, age, ethnicity, gender, and so on. Similarly, the characterization can be performed on collected and analyzed videos of people viewing a news presentation. The characterized cluster profiles can be further analyzed based on demographic data. Various steps in the flow 1200 may be changed in order, repeated, omitted, or the like without departing from the disclosed concepts. Various embodiments of the flow 1200 can be included in a computer program product embodied in a non-transitory computer readable medium that includes code executable by one or more processors. Various embodiments of the flow 1200, or portions thereof, can be included on a semiconductor chip and implemented in special purpose logic, programmable logic, and so on.

Figure 13:
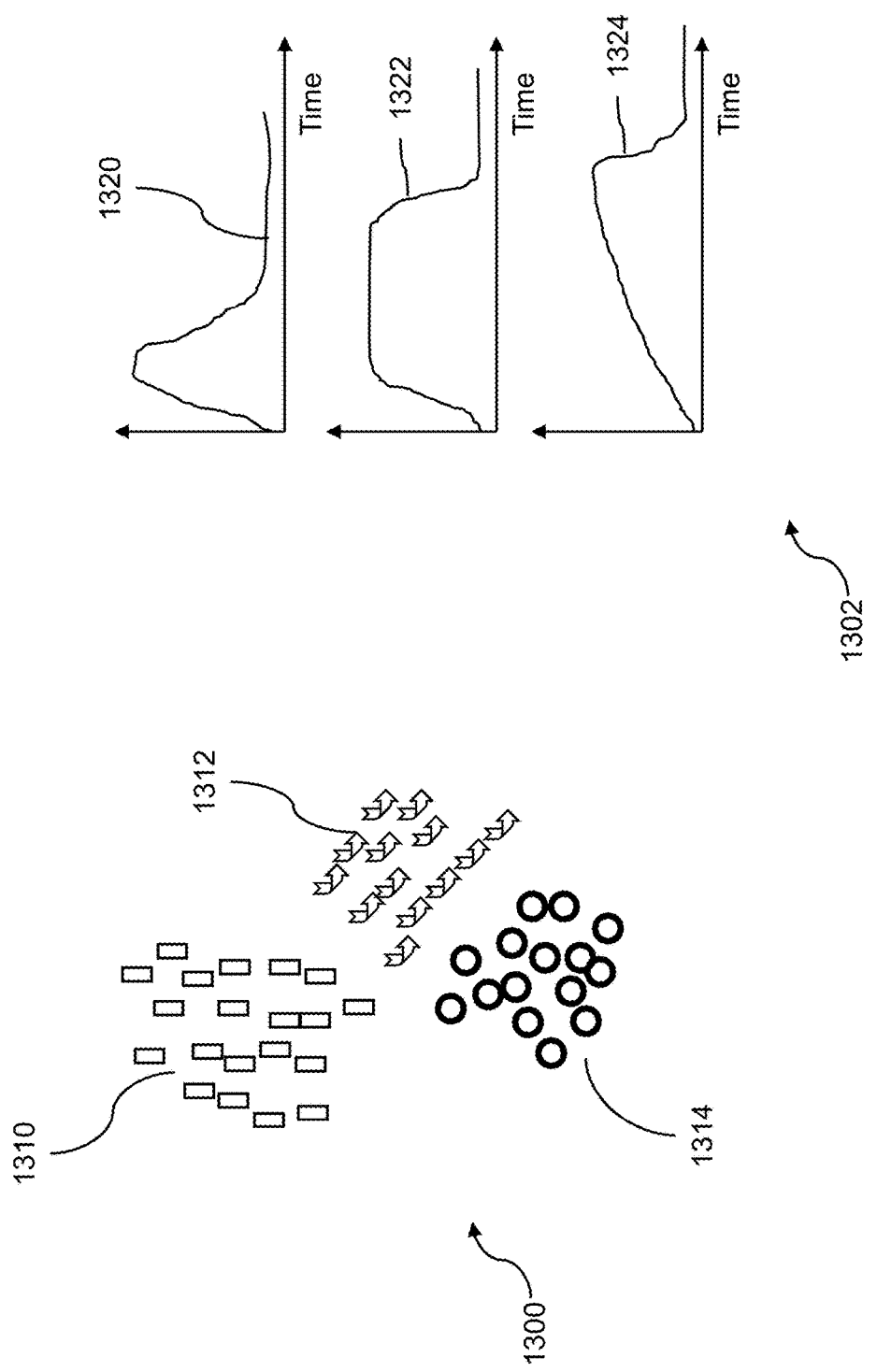
FIG. 13 shows unsupervised clustering of features and characterizations of cluster profiles.

FIG. 13 shows unsupervised clustering of features and characterizations of cluster profiles. The clustering can be accomplished as part of a deep learning effort. The clustering of features and characterizations of cluster profiles can be performed for images collected of an individual. The collected images can be analyzed for mental states and/or facial expressions. A plurality of images can be received of an individual viewing an electronic display. A face can be identified in an image, based on the use of classifiers. The plurality of images can be evaluated to determine mental states and/or facial expressions of the individual. Features including samples of facial data can be clustered using unsupervised clustering. Various clusters can be formed which include similar groupings of facial data observations. The example 1300 shows three clusters, clusters 1310, 1312, and 1314. The clusters can be based on video collected from people who have opted-in to video collection. When the data collected is captured using a web-based framework, the data collection can be performed on a grand scale, including hundreds, thousands, or even more participants who can be located locally and/or across a wide geographic area. Unsupervised clustering is a technique that can be used to process the large amounts of captured facial data and to identify groupings of similar observations. The unsupervised clustering can also be used to characterize the groups of similar observations. The characterizations can include identifying behaviors of the participants. The characterizations can be based on identifying facial expressions and facial action units of the participants. Some behaviors and facial expressions can include faster or slower onsets, faster or slower offsets, longer or shorter durations, etc. The onsets, offsets, and durations can all correlate to time. The data clustering that results from the unsupervised clustering can support data labeling. The labeling can include FACS coding. The clusters can be partially or totally based on a facial expression resulting from participants viewing a video presentation, where the video presentation can be an advertisement, a political message, educational material, a public service announcement, and so on. The clusters can be correlated with demographic information, where the demographic information can include educational level, geographic location, age, gender, income level, and so on.

The cluster profiles 1302 can be generated based on the clusters that can be formed from unsupervised clustering, with time shown on the x-axis and intensity or frequency shown on the y-axis. The cluster profiles can be based on captured facial data including facial expressions. The cluster profile 1320 can be based on the cluster 1310, the cluster profile 1322 can be based on the cluster 1312, and the cluster profile 1324 can be based on the cluster 1314. The cluster profiles 1320, 1322, and 1324 can be based on smiles, smirks, frowns, or any other facial expression. The emotional states of the people who have opted-in to video collection can be inferred by analyzing the clustered facial expression data. The cluster profiles can be plotted with respect to time and can show a rate of onset, a duration, and an offset (rate of decay). Other time-related factors can be included in the cluster profiles. The cluster profiles can be correlated with demographic information, as described above.

Figure 14A:
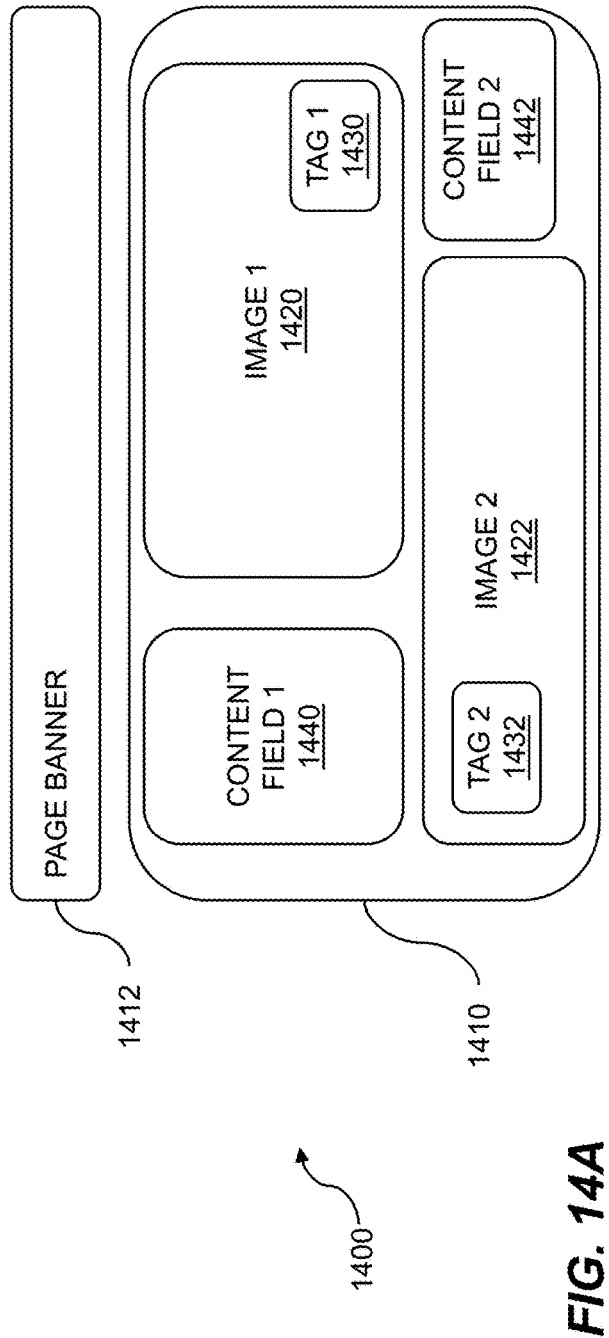
FIG. 14A shows example tags embedded in a webpage.

FIG. 14A shows example tags embedded in a webpage. The tags embedded in the webpage can be used for image analysis for images collected of an individual, and the image analysis can be performed by a multi-layer system. The collected images can be analyzed for mental states and/or facial expressions. A plurality of images can be received of an individual viewing an electronic display. A face can be identified in an image, based on the use of classifiers. The plurality of images can be evaluated to determine mental states and/or facial expressions of the individual. Once a tag is detected, a mobile device, a server, semiconductor based logic, etc. can be used to evaluate associated facial expressions. A webpage 1400 can include a page body 1410, a page banner 1412, and so on. The page body can include one or more objects, where the objects can include text, images, videos, audio, and so on. The example page body 1410 shown includes a first image, image 1 1420; a second image, image 2 1422; a first content field, content field 1 1440; and a second content field, content field 2 1442. In practice, the page body 1410 can contain multiple images and content fields and can include one or more videos, one or more audio presentations, and so on. The page body can include embedded tags, such as tag 1 1430 and tag 2 1432. In the example shown, tag 1 1430 is embedded in image 1 1420, and tag 2 1432 is embedded in image 2 1422. In embodiments, multiple tags are imbedded. Tags can also be imbedded in content fields, in videos, in audio presentations, etc. When a user mouses over a tag or clicks on an object associated with a tag, the tag can be invoked. For example, when the user mouses over tag 1 1430, tag 1 1430 can then be invoked. Invoking tag 1 1430 can include enabling a camera coupled to a user's device and capturing one or more images of the user as the user views a media presentation (or digital experience). In a similar manner, when the user mouses over tag 2 1432, tag 2 1432 can be invoked. Invoking tag 2 1432 can also include enabling the camera and capturing images of the user. In other embodiments, other actions are taken based on invocation of the one or more tags. Invoking an embedded tag can initiate an analysis technique, post to social media, award the user a coupon or another prize, initiate mental state analysis, perform emotion analysis, and so on.

Figure 14B:
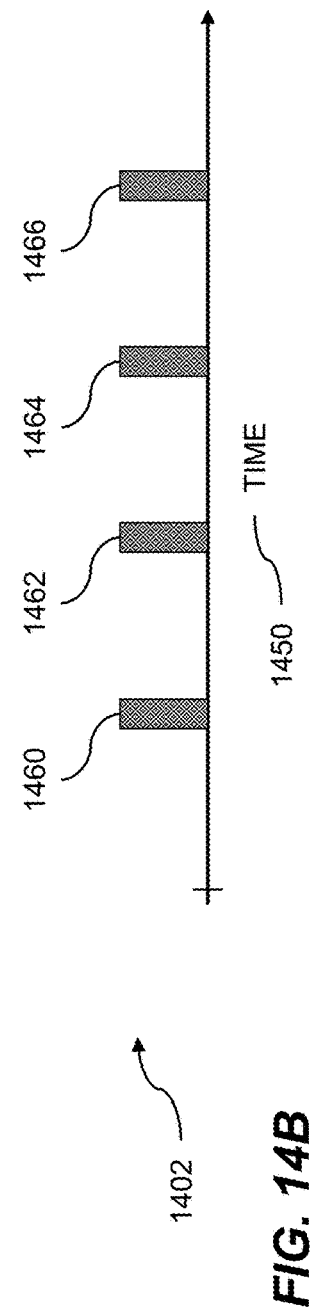
FIG. 14B shows invoking tags to collect images.

FIG. 14B shows invoking tags to collect images. The invoking tags to collect images can be used for image analysis for images collected of an individual. The collected images can be analyzed for mental states and/or facial expressions. A plurality of images can be received of an individual viewing an electronic display. A face can be identified in an image, based on the use of classifiers. The plurality of images can be evaluated to determine mental states and/or facial expressions of the individual. As previously stated, a media presentation can be a video, a webpage, and so on. A video 1402 can include one or more embedded tags, such as a tag 1460, another tag 1462, a third tag 1464, a fourth tag 1466, and so on. In practice, multiple tags can be included in the media presentation. The one or more tags can be invoked during the media presentation. The collection of the invoked tags can occur over time, as represented by a timeline 1450. When a tag is encountered in the media presentation, the tag can be invoked. When the tag 1460 is encountered, invoking the tag can enable a camera coupled to a user device and can capture one or more images of the user viewing the media presentation. Invoking a tag can depend on opt-in by the user. For example, if a user has agreed to participate in a study by indicating an opt-in, then the camera coupled to the user's device can be enabled and one or more images of the user can be captured. If the user has not agreed to participate in the study and has not indicated an opt-in, then invoking the tag 1460 does not enable the camera nor capture images of the user during the media presentation. The user can indicate an opt-in for certain types of participation, where opting-in can be dependent on specific content in the media presentation. The user could opt-in to participation in a study of political campaign messages and not opt-in for a particular advertisement study. In this case, tags that are related to political campaign messages, advertising messages, social media sharing, etc., and that enable the camera and image capture when invoked would be embedded in the media presentation, social media sharing, and so on. However, tags imbedded in the media presentation that are related to advertisements would not enable the camera when invoked. Various other situations of tag invocation are possible.

Figure 15:
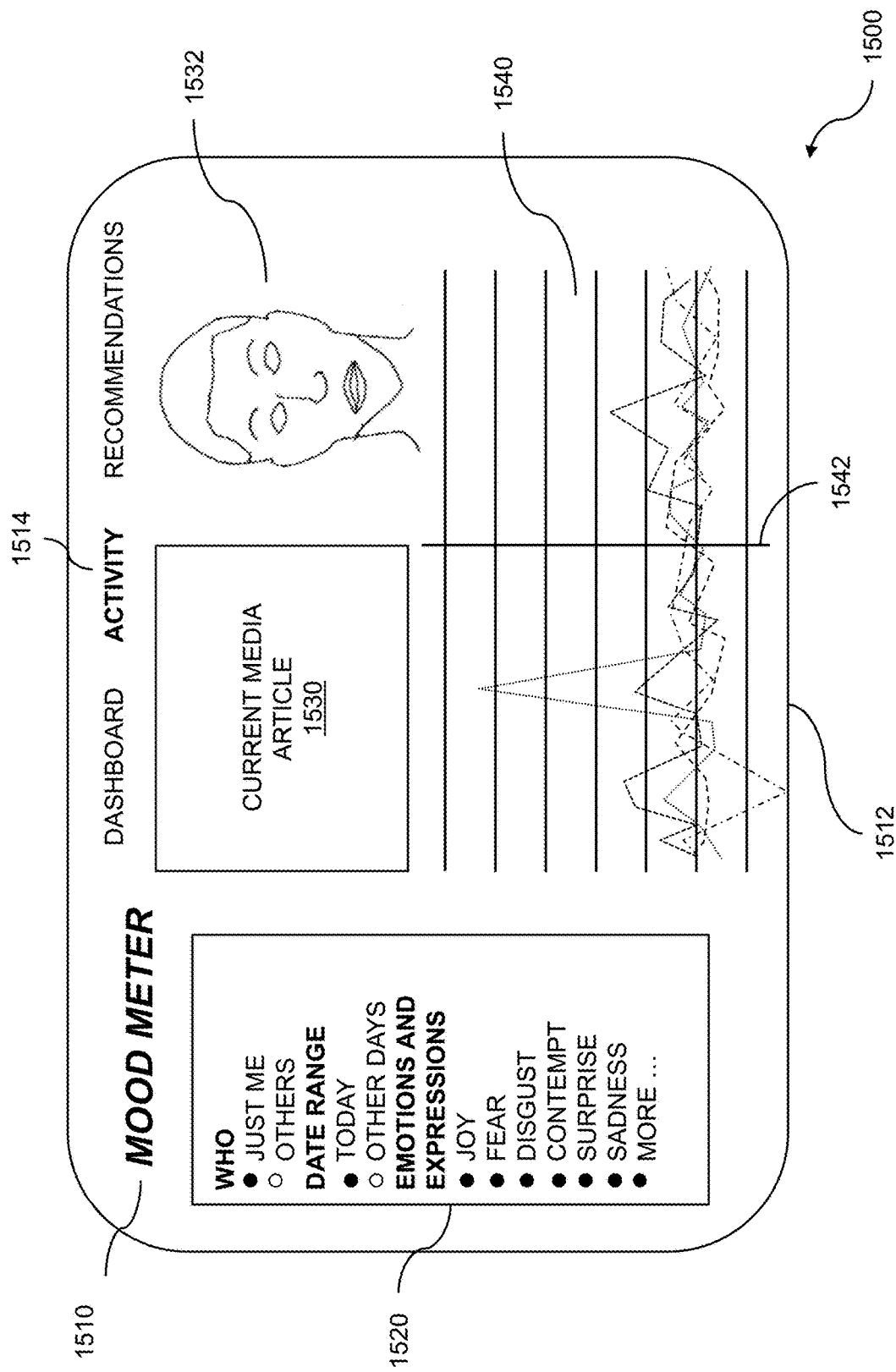
FIG. 15 shows an example mood measurement display for individual activity.

FIG. 15 shows an example mood measurement display for individual activity. A mood measurement for individual activity can be based on mental states inferred from heart rate information and/or facial image analysis. Emotional moods of an individual can be analyzed from mental states. Mental state data and/or facial data can be collected on the individual. The collecting of the mental state data can be accomplished using a webcam or another video capture device, or it can be inferred from heart rate information. Processors are used to analyze the mental state data for providing analysis of the mental state data to the individual in the form of a mood. Mental state data may include many sub-states of emotion, but a mood is a prevailing or overriding emotion or an emotion or mental state of interest, such as overall happiness. Mental state data is inferred and outputted as a mood measurement. An example display 1500, such as an example mood measurement 1510, shows individual activity 1512. The display can include controls 1514 for selecting among various dashboards, displaying activity, recommending ways for improving a mood, and so on. The dashboard can include activity 1520 of the individual and can include the activity of others, a date range, a list of emotions and expressions, selfie settings, screenshot settings, and so on. The display can include an image of a webpage or current media article 1530 being observed by the individual, along with an image of the individual 1532. The display can include moment-by-moment metrics 1540 tracked as a graph over time, including joy, fear, disgust, contempt, surprise, sadness, etc. The moment-by-moment metrics 1540 can include physiological data that can be captured along with the collecting mental state data. The moment-by-moment metrics 1540 can include an indication of a specific point in time 1542, which can be moved along the time axis.

Figure 16:
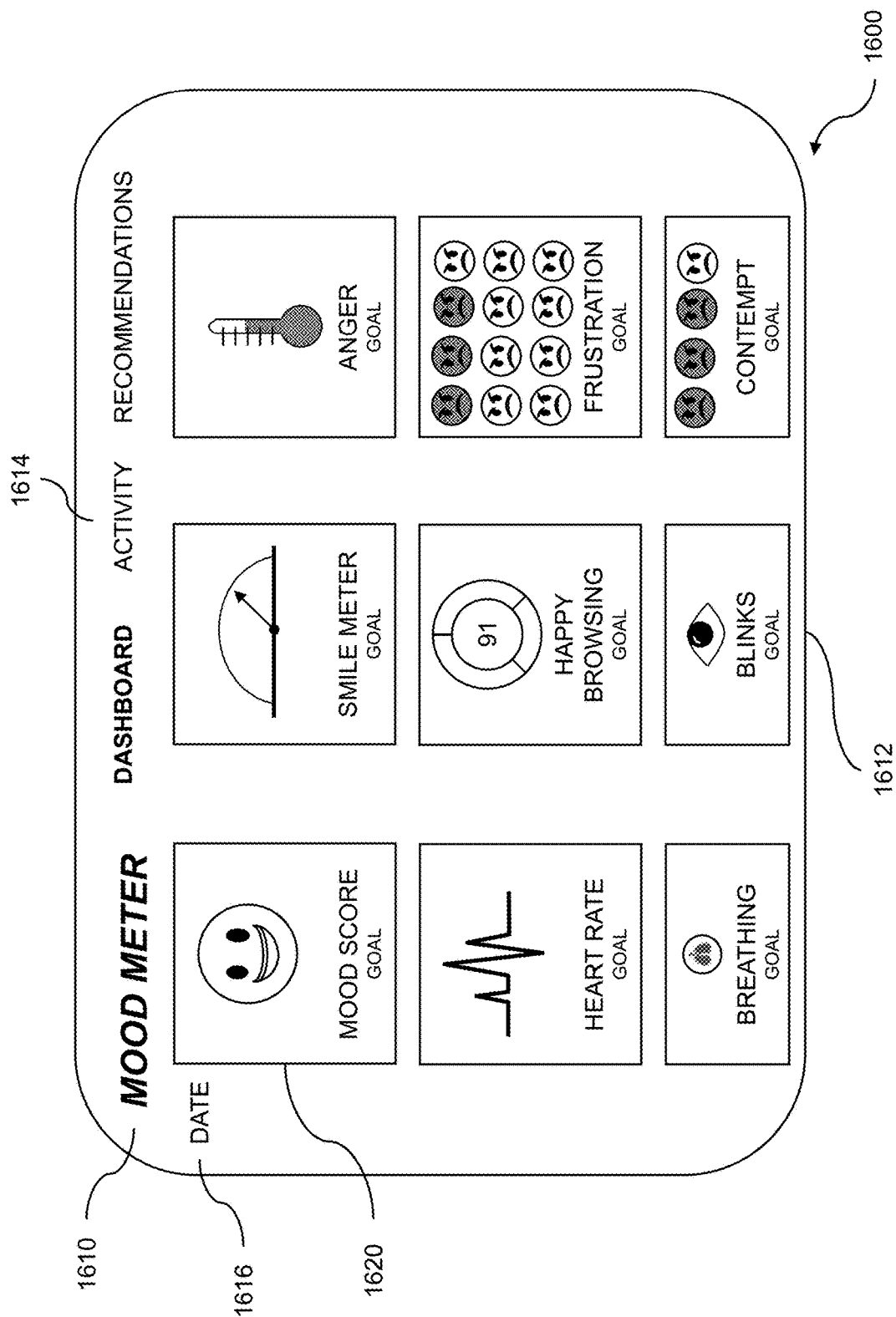
FIG. 16 illustrates an example mood measurement dashboard display.

FIG. 16 illustrates an example mood measurement dashboard display. A dashboard can be used to display information to an individual, where the information is based on inferred mental states from heart rate information and/or facial image analysis. Emotional moods of an individual can be analyzed from mental states. Mental state data and/or facial data can be collected on the individual. The collecting of the mental state data can be accomplished using a webcam or another video capture device, or it can be inferred from heart rate information. Processors are used to analyze the mental state data for providing analysis of the mental state data to the individual in the form of a mood. Mental state data can include many sub-states of emotion, but a mood is a prevailing or overriding emotion or an emotion or mental state of interest, such as overall happiness. Mental state data is inferred and outputted as a mood measurement. An example display 1600, such as example mood measurement 1610, can display individual mood dashboard information 1612 to an individual. A variety of information can be displayed including a mood score 1620, a meter, such as a smile meter and a target number of smiles per day, an anger meter with daily goal, a heart rate with daily goal, a browsing mood such as happy browsing with a daily goal, a frustration meter and goal, a breathing meter and goal, an eye blinks meter and goal, a contempt meter and goal, and so on. The dashboard 1612 can include controls 1614 which can be used to select among multiple dashboards, to display various activities, to take action or receive suggestions for such activities as improving a mood, and so on. A selectable date 1616 can be employed to display moods for various days in the past.

Figure 17:
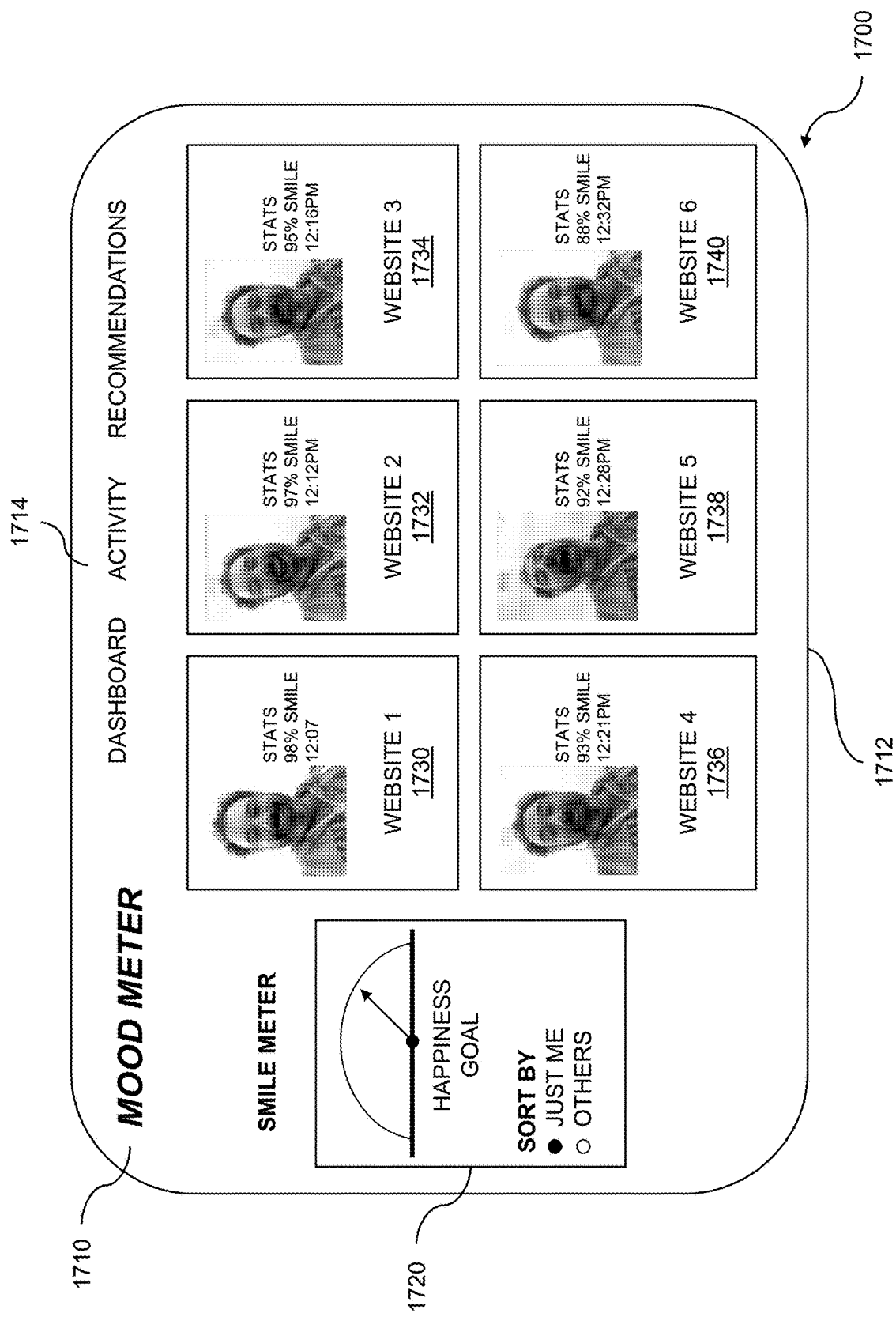
FIG. 17 illustrates example mood measurement statistical results.

FIG. 17 illustrates example mood measurement statistical results. Various statistical results can be displayed for an individual, where the information is based on inferred mental states from heart rate information and/or facial image analysis. Emotional moods of an individual can be analyzed from mental states. Mental state data and/or facial data can be collected on the individual. The collecting of the mental state data can be accomplished using a webcam or another video capture device, or it can be inferred from heart rate information. Processors are used to analyze the mental state data for providing analysis of the mental state data to the individual in the form of a mood. Mental state data can include many sub-states of emotion, but a mood is a prevailing or overriding emotion or an emotion or mental state of interest, such as overall happiness. Mental state data is inferred and outputted as a mood measurement. Statistical results 1700 based on analyzing and evaluating can be displayed to an individual using a mood measurement display 1710. The display can show statistical results for a variety of moods such as happy, sad, confused, angry, annoyed, concentrating, bored, and so on. The display can show statistical results based on a variety of emotions, mental states, etc. The displayed moods, emotions, mental states, and so on, can be based on aggregating the mental state data from the individual with mental state data from other individuals. The mental state data for the individual can be compared to the aggregated mental state data from the other individuals. The mental state data from other individuals can be based on demographics. The display 1710 can show individual mood statistics 1712. The statistics 1712 can be related to an emotional or mood goal, such as a smile meter/happiness goal 1720. Controls 1714 can be used to select various views, activities, actions, and so on. The display 1710, when displaying smiles, can include a smile meter 1720. The smile meter can include a display for level of happiness, a goal, sorting options such as the most recent smile and biggest smiles, selfie settings, screenshot settings, etc. The statistical results of a mood such as a smile can be displayed with various statistics associated with various visited websites or media or games 1730, 1732, 1734, 1736, 1738, and 1740. The statistics can include a percentage of time smiling, the time at which the smile occurred, the website or media or game for which the smile occurred, an image of the individual for whom the statistical results are being displayed, etc. Several renderings of statistics can be displayed simultaneously.

Figure 18:
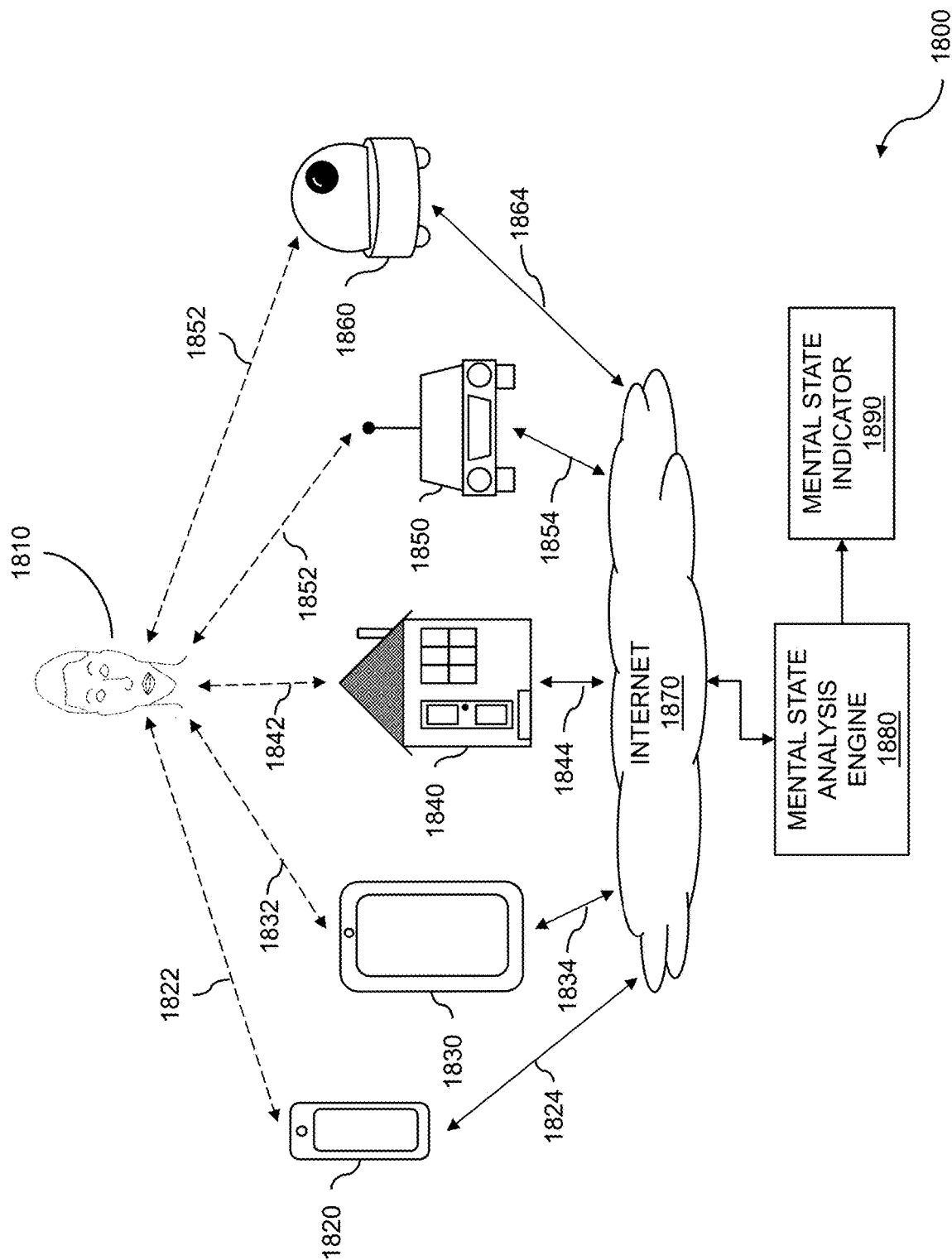
FIG. 18 illustrates mental state analysis using connected computer-based devices.

FIG. 18 illustrates mental state analysis using one or more connected, computer-based devices. In illustration 1800, an individual 1810 can interact with many different kinds of computer-based devices 1820, 1830, 1840, 1850, and 1860. The various computer-based devices can be used to obtain video of the individual 1810 and, in embodiments, analyze the video to obtain heart rate information. For example, mobile phone 1820 can have line of sight 1822 from one or more integrated cameras to individual 1810 for purposes of obtaining video of the individual; tablet 1830 can have line of sight 1832 from one or more integrated cameras to individual 1810 for purposes of obtaining video of the individual; smart house 1840 can have line of sight 1842 from one or more integrated cameras to individual 1810 for purposes of obtaining video of the individual; smart automobile 1850 can have line of sight 1852 from one or more integrated cameras to individual 1810 for purposes of obtaining video of the individual; social robot 1860 can have line of sight 1852 from one or more integrated cameras to individual 1810 for purposes of obtaining video of the individual. The integrated cameras of computer-based devices 1820, 1830, 1840, 1850, and 1860 can be webcams. As the term is used herein, webcams can refer to a camera on a computer (such as a laptop, a net-book, a tablet, a wearable device, or the like), a video camera, a still camera, a cell phone camera, a camera mounted in a transportation vehicle, a wearable device including a camera, a mobile device camera (including, but not limited to, a front side camera), a thermal imager, a CCD device, a three-dimensional camera, a depth camera, a social robot camera, multiple webcams used to capture different views of individuals, or any other type of image capture apparatus that allows image data to be captured and used by an electronic system.

Illustration 1800 includes a computing network, such as the Internet 1870, connected to the various computer-based devices. For example, device 1820 is connected to the Internet 1870 over network link 1824; device 1830 is connected to the Internet 1870 over network link 1834; device 1840 is connected to the Internet 1870 over network link 1844; device 1850 is connected to the Internet 1870 over network link 1854; device 1860 is connected to the Internet 1870 over network link 1864. The network link can be a wireless link, a wired link, and so on. Through a network, such as the Internet 1870, a mental state analysis engine 1880 can receive the video obtain by computer-based devices 1820, 1830, 1840, 1850, and 1860 for processing and analysis. The analysis can be to determine heart rate information. The analysis can includes: identifying a face of the individual in a portion of the video; separating pixels from the video of the individual, into at least a green pixel temporal intensity trace; training a statistical classifier, wherein the training is learned from a data set consisting of human blood volume pulse synchronized face videos; and recognizing a pulse, from the video of the individual, using the statistical classifier, by learning patterns of variability in the mean of the pixel temporal intensity trace. The heart rate information is correlated to a stimulus that the individual is encountering. Mental states of the individual are inferred, using one or more processors of mental state analysis engine 1880, based on the heart rate information. A mental state indicator 1890 can be the result. In embodiments, a mood measurement based on the mental states which were inferred is outputted.

Figure 19:
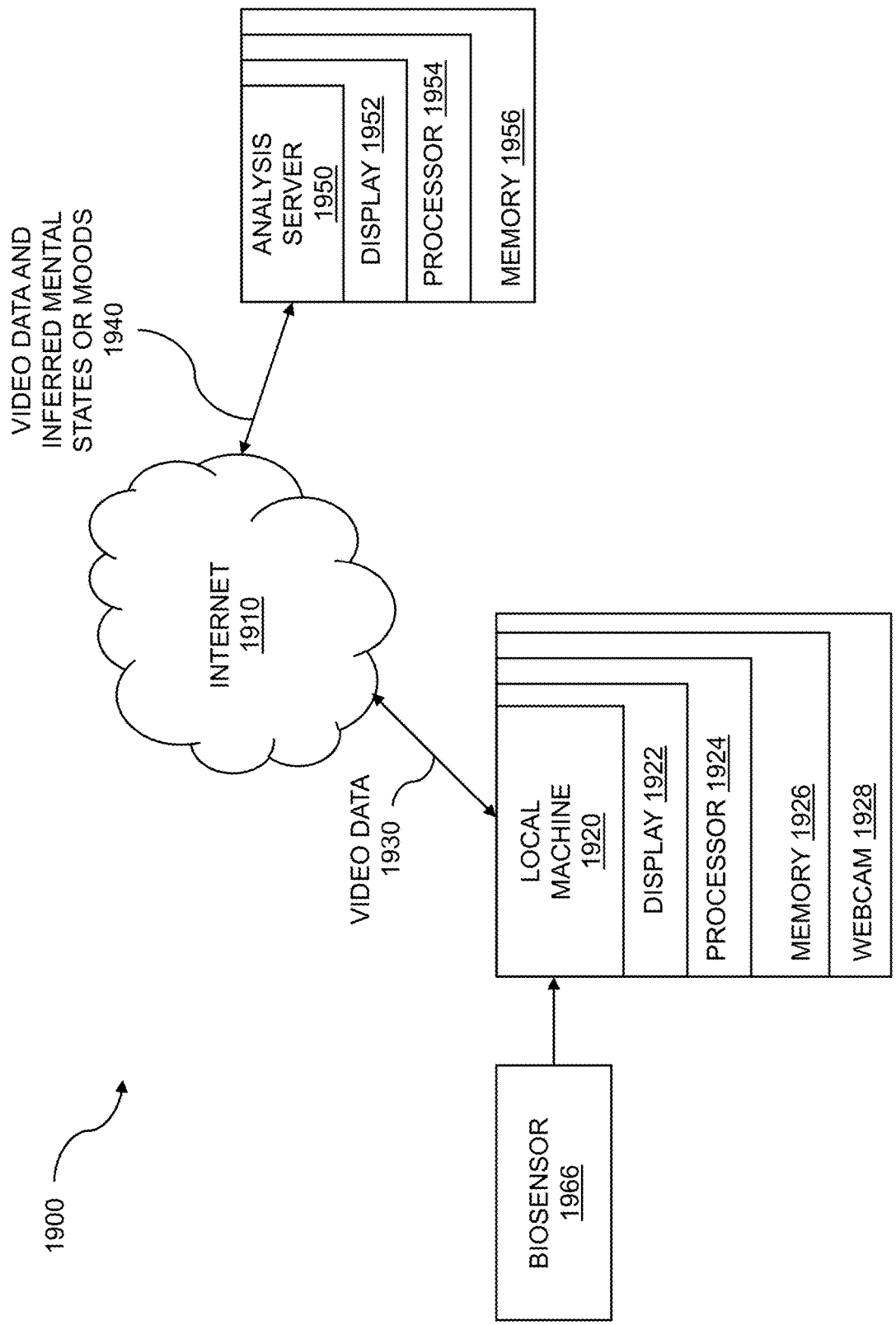
FIG. 19 is a system diagram for mental state analysis.

FIG. 19 is a system diagram for mental state analysis. The system 1900 can include a local machine 1920 with which an individual is interacting. The local machine 1920 can include one or more processors 1924 coupled with a memory 1926 that can be used to store instructions and data. In some embodiments, the local machine 1920 is a mobile device, including, but not limited to, a laptop, a personal computer, a tablet computer, a cell phone, a smart phone, a vehicle mounted computer, an in-vehicle computer, a social robot, a wearable computer, and so on. The local machine 1920 can also include a display 1922 which can be used to show a stimulus to the individual, such as a website, a media presentation, a game, or a computer program user interface. The display 1922 can be any electronic display, including but not limited to a computer display, a laptop screen, a net-book screen, a tablet screen, a cell phone display, a mobile device display, an automotive type display, a remote with a display, a television, a projector, or the like. The local machine can also include a webcam 1928 capable of capturing video and still images of the user interacting with the local machine 1920. The webcam 1928, as the term is used herein, can refer to a camera on a computer (such as a laptop, a net-book, a tablet, a wearable device, or the like), a video camera, a still camera, a cell phone camera, a camera mounted in a transportation vehicle, a wearable device including a camera, a mobile device camera (including, but not limited to, a front side camera), a thermal imager, a CCD device, a three-dimensional camera, a depth camera, a social robot camera, multiple webcams used to capture different views of viewers, or any other type of image capture apparatus that allows image data to be captured and used by an electronic system. In some embodiments, one or more biosensors 1966 are coupled to the local machine 1920. The biosensor or biosensors 1966 can monitor the individual interacting with the local machine 1920 to obtain physiological information on the individual.

The one or more processors 1924 can be configured to obtain video of the individual using the webcam or other camera; analyze the video to determine heart rate information; and infer mental states of the individual based, at least in part and in some embodiments, on the heart rate information. In embodiments, the system comprises a computer program product embodied in a non-transitory computer readable medium for mental state analysis, the computer program product comprising code for: obtaining video of an individual; analyzing the video to determine heart rate information, wherein the analyzing includes: identifying a face of the individual in a portion of the video; separating pixels from the video of the individual, into at least a green pixel temporal intensity trace; training a statistical classifier, wherein the training is learned from a data set consisting of human blood volume pulse synchronized face videos; and recognizing a pulse, from the video of the individual, using the statistical classifier, by learning patterns of variability in the mean of the pixel temporal intensity trace; correlating the heart rate information to a stimulus that the individual is encountering; and inferring mental states of the individual based on the heart rate information.

Some embodiments include an analysis server 1950, although some embodiments comprise performing the analysis of the video data, inferring mental states, and executing other aspects of methods described herein on the local machine 1920. The local machine 1920 sends video data 1930 over the Internet 1910 or another computer communication link to the analysis server 1950, in some embodiments. In some embodiments, the analysis server 1950 is provisioned as a web service. The analysis server 1950 includes one or more processors 1954 coupled to a memory 1956 to store instructions and/or data. Some embodiments of the analysis server 1950 include a display 1952. The one or more processors 1954 can be configured to receive video data and send inferred mental states and/or moods 1940 from/to the local machine 1920 or another machine over the Internet 1910. Thus, the obtaining the video of the individual can comprise receiving the video from another computer, and the obtaining the video of the individual can comprise receiving the video over the Internet. The transfer of video can be accomplished once an entire video is captured of a person for analysis. Alternatively, video can be streamed as it is collected. The video can be analyzed for heart rate information on the fly as the video is collected or as it is streamed to analysis machine. The one or more processors 1954 can also be configured to analyze the video 1940 to determine heart rate information; and infer mental states of the individual based on the heart rate information. In some embodiments, the analysis server receives video of multiple individuals from multiple other computers, and determines heart rate information for the multiple individuals. In some embodiments, the heart rate information from the multiple individuals is aggregated to determine an aggregated mental state of the group including the multiple individuals.

Each of the above methods may be executed on one or more processors on one or more computer systems. Embodiments may include various forms of distributed computing, client/server computing, and cloud based computing. Further, it will be understood that the depicted steps or boxes contained in this disclosure's flow charts are solely illustrative and explanatory. The steps may be modified, omitted, repeated, or re-ordered without departing from the scope of this disclosure. Further, each step may contain one or more sub-steps. While the foregoing drawings and description set forth functional aspects of the disclosed systems, no particular implementation or arrangement of software and/or hardware should be inferred from these descriptions unless explicitly stated or otherwise clear from the context. All such arrangements of software and/or hardware are intended to fall within the scope of this disclosure.

The block diagrams and flowchart illustrations depict methods, apparatus, systems, and computer program products. The elements and combinations of elements in the block diagrams and flow diagrams, show functions, steps, or groups of steps of the methods, apparatus, systems, computer program products and/or computer-implemented methods. Any and all such functions—generally referred to herein as a "circuit," "module," or "system"—may be implemented by computer program instructions, by special-purpose hardware-based computer systems, by combinations of special purpose hardware and computer instructions, by combinations of general purpose hardware and computer instructions, and so on.

A programmable apparatus which executes any of the above mentioned computer program products or computer-implemented methods may include one or more microprocessors, microcontrollers, embedded microcontrollers, programmable digital signal processors, programmable devices, programmable gate arrays, programmable array logic, memory devices, application specific integrated circuits, or the like. Each may be suitably employed or configured to process computer program instructions, execute computer logic, store computer data, and so on.

It will be understood that a computer may include a computer program product from a computer-readable storage medium and that this medium may be internal or external, removable and replaceable, or fixed. In addition, a computer may include a Basic Input/Output System (BIOS), firmware, an operating system, a database, or the like that may include, interface with, or support the software and hardware described herein.

Embodiments of the present invention are neither limited to conventional computer applications nor the programmable apparatus that run them. To illustrate: the embodiments of the presently claimed invention could include an optical computer, quantum computer, analog computer, or the like. A computer program may be loaded onto a computer to produce a particular machine that may perform any and all of the depicted functions. This particular machine provides a means for carrying out any and all of the depicted functions.

Any combination of one or more computer readable media may be utilized including but not limited to: a non-transitory computer readable medium for storage; an electronic, magnetic, optical, electromagnetic, infrared, or semiconductor computer readable storage medium or any suitable combination of the foregoing; a portable computer diskette; a hard disk; a random access memory (RAM); a read-only memory (ROM), an erasable programmable read-only memory (EPROM, Flash, MRAM, FeRAM, or phase change memory); an optical fiber; a portable compact disc; an optical storage device; a magnetic storage device; or any suitable combination of the foregoing. In the context of this document, a computer readable storage medium may be any tangible medium that can contain or store a program for use by or in connection with an instruction execution system, apparatus, or device.

It will be appreciated that computer program instructions may include computer executable code. A variety of languages for expressing computer program instructions may include without limitation C, C++, Java, JavaScript™, ActionScript™, assembly language, Lisp, Perl, Tcl, Python, Ruby, hardware description languages, database programming languages, functional programming languages, imperative programming languages, and so on. In embodiments, computer program instructions may be stored, compiled, or interpreted to run on a computer, a programmable data processing apparatus, a heterogeneous combination of processors or processor architectures, and so on. Without limitation, embodiments of the present invention may take the form of web-based computer software, which includes client/server software, software-as-a-service, peer-to-peer software, or the like.

In embodiments, a computer may enable execution of computer program instructions including multiple programs or threads. The multiple programs or threads may be processed approximately simultaneously to enhance utilization of the processor and to facilitate substantially simultaneous functions. By way of implementation, any and all methods, program codes, program instructions, and the like described herein may be implemented in one or more threads which may in turn spawn other threads, which may themselves have priorities associated with them. In some embodiments, a computer may process these threads based on priority or other order.

Unless explicitly stated or otherwise clear from the context, the verbs "execute" and "process" may be used interchangeably to indicate execute, process, interpret, compile, assemble, link, load, or a combination of the foregoing. Therefore, embodiments that execute or process computer program instructions, computer-executable code, or the like may act upon the instructions or code in any and all of the ways described. Further, the method steps shown are intended to include any suitable method of causing one or more parties or entities to perform the steps. The parties performing a step, or portion of a step, need not be located within a particular geographic location or country boundary. For instance, if an entity located within the United States causes a method step, or portion thereof, to be performed outside of the United States then the method is considered to be performed in the United States by virtue of the causal entity.

While the invention has been disclosed in connection with preferred embodiments shown and described in detail, various modifications and improvements thereon will become apparent to those skilled in the art. Accordingly, the forgoing examples should not limit the spirit and scope of the present invention; rather it should be understood in the broadest sense allowable by law.

What is claimed is:

1. A computer-implemented method for mental state analysis comprising:
    obtaining video of an individual;
    analyzing the video to determine heart rate information, wherein the analyzing includes:
        identifying a face of the individual in a portion of the video;
        separating pixels from the video of the individual, into at least a green pixel temporal intensity trace;
        training a statistical classifier, wherein the training is learned from a data set consisting of human blood volume pulse synchronized face videos; and recognizing a pulse, from the video of the individual, using the statistical classifier, by learning patterns of variability in the mean of the pixel temporal intensity trace;

correlating the heart rate information to a stimulus that the individual is encountering; and inferring, using one or more processors, mental states of the individual based on the heart rate information.

2. The method of claim 1 further comprising outputting a mood measurement based on the mental states which were inferred.

3. The method of claim 1 further comprising analyzing a media presentation based on the mental states which were inferred.

4. The method of claim 3 wherein the analyzing a media presentation is further based on learning about heart rate information.

5. The method of claim 4 wherein the learning further comprises factoring in one or more previous frames of data of the video.

6. The method of claim 5 further comprising capturing heart rate signal fluctuations in the video due to blood flow.

7. The method of claim 1 further comprising aggregating the heart rate information for the individual with other people.

8. The method of claim 1 further comprising aggregating the mental states for the individual with other people.

9. The method of claim 1 wherein learning about heart rate information is included as part of the analyzing.

10. The method of claim 1 wherein the inferring includes determining arousal, attention, or valence.

11. The method of claim 1 wherein the analyzing includes calculating blood volume pulse.

12. The method of claim 1 wherein the analyzing factors in an occlusion of part of a face for the individual.

13. The method of claim 1 further comprising determining contextual information.

14. The method of claim 1 further comprising evaluating a temporal signature for the mental states.

15. The method of claim 14 further comprising using the temporal signature to infer additional mental states.

16. The method of claim 1 wherein the inferring mental states further comprises analyzing an emotional mood of the individual.

17. The method of claim 16 wherein the analyzing the emotional mood of the individual is used to enable the individual to track emotional health.

18. The method of claim 1 further comprising performing unsupervised learning, as part of the training, for pulse recognition.

19. The method of claim 1 further comprising learning image descriptors, as part of the training, for emotional content.

20. The method of claim 1 further comprising establishing a region of interest including the face, separating pixels in the region of interest into at least two channel values and combining to form raw traces, transforming and decomposing the raw traces into at least one independent source signal, and processing the at least one independent source signal to obtain the heart rate information.

21. The method of claim 20 wherein the heart rate information includes heart rate and the heart rate is determined based on changes in an amount of reflected light.

22. The method of claim 1 wherein the video includes a plurality of other people.

23. The method of claim 22 further comprising identifying faces of the plurality of other people and analyzing the video to determine heart rate information on the plurality of other people.

24. The method of claim 23 further comprising inferring mental states of the plurality of other people based on the heart rate information on the plurality of other people.

25. The method of claim 1 further comprising obtaining biosensor data for the individual.

26. The method of claim 25 wherein the biosensor data augments the heart rate information.

27. The method of claim 25 wherein the biosensor data includes one or more of electrodermal activity, heart rate, heart rate variability, skin temperature, or respiration.

28. A computer program product embodied in a non-transitory computer readable medium for mental state analysis, the computer program product comprising code which causes one or more processors to perform operations of:

obtaining video of an individual;

analyzing the video to determine heart rate information, wherein the analyzing includes:

identifying a face of the individual in a portion of the video;

separating pixels from the video of the individual, into at least a green pixel temporal intensity trace;

training a statistical classifier, wherein the training is learned from a data set consisting of human blood volume pulse synchronized face videos; and recognizing a pulse, from the video of the individual, using the statistical classifier, by learning patterns of variability in the mean of the pixel temporal intensity trace;

correlating the heart rate information to a stimulus that the individual is encountering; and inferring mental states of the individual based on the heart rate information.

29. A computer system for mental state analysis comprising:

a memory which stores instructions;

one or more processors attached to the memory wherein the one or more processors, when executing the instructions which are stored, are configured to:

obtain video of an individual;

analyze the video to determine heart rate information, wherein analyzing includes:

identifying a face of the individual in a portion of the video;

separating pixels from the video of the individual into at least a green pixel temporal intensity trace;

training a statistical classifier, wherein the training is learned from a data set consisting of human blood volume pulse synchronized face videos; and recognizing a pulse, from the video of the individual, using the statistical classifier, by learning patterns of variability in the mean of the pixel temporal intensity trace;

correlate the heart rate information to a stimulus that the individual is encountering; and infer mental states of the individual based on the heart rate information.

* * * * *